(12) United States Patent
Roessler

(10) Patent No.: US 11,946,838 B2
(45) Date of Patent: Apr. 2, 2024

(54) CALIBRATION SLIDES FOR DIGITAL PATHOLOGY

(71) Applicant: Ventana Medical Systems, Inc., Tucson, AZ (US)

(72) Inventor: Christian Roessler, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 340 days.

(21) Appl. No.: 17/374,859

(22) Filed: Jul. 13, 2021

(65) Prior Publication Data

US 2022/0003639 A1 Jan. 6, 2022

Related U.S. Application Data

(63) Continuation of application No. PCT/EP2020/051848, filed on Jan. 27, 2020.

(60) Provisional application No. 62/798,595, filed on Jan. 30, 2019.

(51) Int. Cl.
*G01N 1/28* (2006.01)
*C08J 3/075* (2006.01)

(52) U.S. Cl.
CPC ............... *G01N 1/28* (2013.01); *C08J 3/075* (2013.01); *C08J 2205/022* (2013.01); *C08J 2333/06* (2013.01); *G01N 2001/2893* (2013.01)

(58) Field of Classification Search
CPC ............ C12Q 2326/00; C12Q 2561/00; G01N 2496/00; G01N 2496/25; G01N 2600/00
See application file for complete search history.

(56) References Cited

U.S. PATENT DOCUMENTS

| 3,876,504 A | 4/1975 | Koffler |
| 5,087,421 A | 2/1992 | Koyama et al. |

FOREIGN PATENT DOCUMENTS

| EP | 0264079 A2 | 4/1988 | |
| EP | 0269979 A2 | 6/1988 | |
| GB | 2524227 A | 9/2015 | |
| WO | 2012070041 A1 | 5/2012 | |
| WO | 2013186530 A1 | 12/2013 | |
| WO | WO-2021242637 A1 * | 12/2021 | ............... G01N 1/30 |

OTHER PUBLICATIONS

International Search Report and Written Opinion dated Jul. 30, 2020 in connection with PCT/EP2020/051848 filed Jan. 27, 2020, 19 pages.

* cited by examiner

*Primary Examiner* — Don K Wong
(74) *Attorney, Agent, or Firm* — Charney IP Law LLC; Thomas M. Finetti

(57) ABSTRACT

In some embodiments, the present disclosure is directed to coatings or thin films comprising a dye or stain embedded within a matrix, e.g. a polymer matrix.

20 Claims, 18 Drawing Sheets

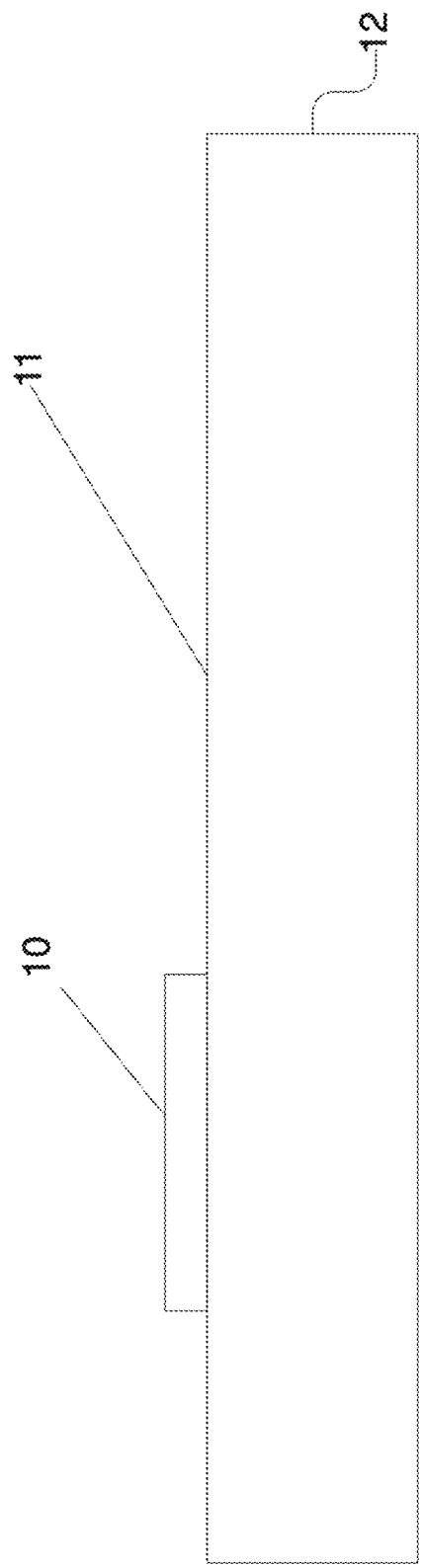

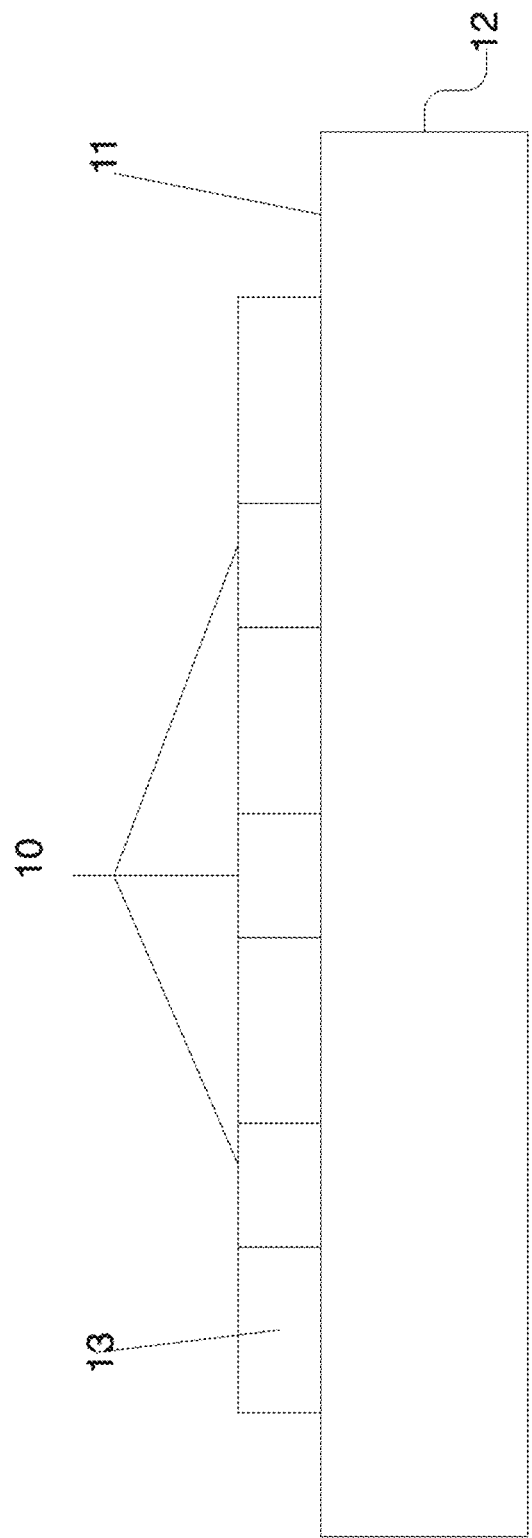

CALIBRATION SLIDES FOR DIGITAL PATHOLOGY

CROSS-REFERENCE TO RELATED APPLICATIONS

The present application is a continuation of International Application No. PCT/EP2020/051848 filed on Jan. 27, 2020, which application claims the benefit of the filing date of U.S. Provisional Patent Application No. 62/798,595 filed on Jan. 30, 2019. Each of the aforementioned applications are hereby incorporated by reference herein in their entireties.

BACKGROUND OF THE DISCLOSURE

Digital pathology involves scanning of whole histopathology or cytopathology glass slides into digital images interpretable on a computer screen. These images are to be processed subsequently by an imaging algorithm or interpreted by a pathologist. In order to examine tissue sections (which are virtually transparent), tissue sections are prepared using colored histochemical stains that bind selectively to cellular components. Color-enhanced, or stained, cellular structures are used by clinicians or a computer-aided diagnosis (CAD) algorithm to identify morphological markers of a disease, and to proceed with therapy accordingly. Observing the assay enables a variety of processes, including diagnosis of disease, assessment of response to treatment, and development of new drugs to fight disease.

Immunohistochemical (IHC) slide staining can be utilized to identify proteins in cells of a tissue section and hence is widely used in the study of different types of cells, such as cancerous cells and immune cells in biological tissue. Thus, IHC staining may be used in research to understand the distribution and localization of the differentially expressed biomarkers of immune cells (such as T-cells or B-cells) in a cancerous tissue for an immune response study. For example, tumors often contain infiltrates of immune cells, which may prevent the development of tumors or favor the outgrowth of tumors.

In-situ hybridization (ISH) can be used to look for the presence of a genetic abnormality or condition such as amplification of cancer causing genes specifically in cells that, when viewed under a microscope, morphologically appear to be malignant. In situ hybridization (ISH) employs labeled DNA or RNA probe molecules that are anti-sense to a target gene sequence or transcript to detect or localize targeted nucleic acid target genes within a cell or tissue sample. ISH is performed by exposing a cell or tissue sample immobilized on a glass slide to a labeled nucleic acid probe which is capable of specifically hybridizing to a given target gene in the cell or tissue sample. Several target genes can be simultaneously analyzed by exposing a cell or tissue sample to a plurality of nucleic acid probes that have been labeled with a plurality of different nucleic acid tags. By utilizing labels having different emission wavelengths, simultaneous multicolored analysis may be performed in a single step on a single target cell or tissue sample.

BRIEF SUMMARY OF THE DISCLOSURE

Newer assays require semi-quantitative and quantitative measurements of stain signals to provide a clinical diagnosis. Often imaging systems are used for both gathering the images of the stained slide and quantifying the stain signal. Most imaging systems are composed of standard microscopy lens arrays that take a white light source (e.g. LED, incandescent, halogen, etc.), pass it through the sample, and then collect the transmitted light on a CCD or CMOS camera sensor. The imaging setup described herein produces signals that vary non-linearly depending on the exact illumination source, illumination pathway, and the camera sensor. It is necessary to calibrate the resulting sample image to take into account this non-linearity. One other source of non-linearity can come from the sample itself, namely a dye or chromogen that does not obey the Beer-Lambert law of light extinction. Given the myriad of hardware configurations in use on commercial imaging systems, not to mention fluctuations in hardware (i.e. CCD or CMOS sensor) performance from a single manufacturer and the use of multiple dyes or chromogens that do not obey the Beer-Lambert law, in situ calibration with the exact dye or chromogen of interest is the only way to ensure accurate signal measurements on an imaging system.

It is believed that the Beer-Lambert equation assumes small stain concentrations and no interaction between the absorbing molecules. This assumption, however, does not hold well for concentration dependent stains, such as DAB, due to its precipitate-forming reaction during sample processing. Besides absorption, scattering also contributes to the light extinction process which causes a non-linear relation between the optical density value and the stain amount. In view of this, it is believed that concentration dependent stains, such as DAB, present different chromatic properties at different concentrations.

Accordingly, Applicants have developed calibration coatings and calibration slides such that optimal color reference vectors for concentration dependent stains, such as DAB or Fast Red, may be derived, such as at varying concentrations. In some embodiments, the derived color reference vectors may be used for unmixing acquired multispectral image data, wherein the optimal color reference vector for the dye or stain is selected from a set of color reference vectors for the dye or stain, each color reference vector within the set of color reference vectors describing or characterizing the dye or stain at a different concentration level (e.g. 1×, 2×, 4×, 8×, etc.).

In view of the foregoing, the present disclosure provides, in some aspects, calibration slides having concentration-specific amounts of a dye or stain, such as DAB or Fast Red. In some embodiments, the calibration slides are used to derive color reference vectors for the dye or stain as noted above. In some embodiments, the calibration slides comprise a dye or stain uniformly embedded or dispersed within a matrix, such as a polymer matrix. In some embodiments, the dye or stain uniformly embedded or dispersed within the matrix is present in a coating or thin film disposed on the surface of a substrate, such as an optically transparent substrate. In some embodiments, the optically transparent substrate is a microscope slide.

In one aspect of the present disclosure is a calibration system comprising: an optically transparent substrate; a film having a substantially uniform thickness disposed on at least a portion of the optically transparent substrate, the film comprising a chromogenic precipitate embedded within a polymer, and wherein the chromogenic precipitate is uniformly dispersed within the polymer. In some embodiments, the polymer is a hydrogel. In some embodiments, the hydrogel comprises crosslinked gelatin. In some embodiments, the crosslinked gelatin is derived from gelatin and an aldehyde. In some embodiments, the hydrogel is derived from a gelling agent and a crosslinking agent. In some embodiments, the polymer is an acrylate.

In some embodiments, the chromogenic precipitate is a reaction product of a chromogen and an enzyme. In some embodiments, the chromogen is selected from the group consisting of 5-Bromo-4-Chloro-3-Indolyl Phosphate; 4-Chloro-2-methyl benzenediazonium; 3,3'-Diaminobenzidine; 3,3',5,5;-tetramethylbenzidine; 4-chloro-1-naphthol; 2,2,Äs-azino-bis(3-ethylbenzothiazoline-6-sulphonic acid); o-phenylenediamine dihydrochloride; p-Nitrophenyl Phosphate; 5-Bromo-4-Chloro-3-indolyl-B-D-Galactopyranoside; and 2,2,5-5-tetra-p-nitrophenyl-3,3-(3,3-dimethoxy-4,4-biphenylene)-di tetrazolium chloride. In some embodiments, the chromogen is 3,3'-Diaminobenzidine. In some embodiments, the enzyme is selected from the group consisting of alkaline phosphatase, horse radish peroxidase, glycosylases, and glucose oxidase. In some embodiments, a ratio of the chromogenic precipitate to the polymer ranges from about 0.1 to about 100. In other embodiments, a ratio of the chromogenic precipitate to the polymer ranges from about 0.1 to about 80. In yet other embodiments, a ratio of the chromogenic precipitate to the polymer ranges from about 0.1 to about 60. In further embodiments, a ratio of the chromogenic precipitate to the polymer ranges from about 0.1 to about 40. In yet further embodiments, a ratio of the chromogenic precipitate to the polymer ranges from about 0.1 to about 20. In other embodiments, a ratio of the chromogenic precipitate to the polymer ranges from about 0.1 to about 10. In yet other embodiments, a ratio of the chromogenic precipitate to the polymer ranges from about 0.1 to about 5.

In another aspect of the present disclosure is a set of slides comprising: a first slide having a first coating disposed on at least a portion of an upper surface of the first slide, the first coating comprising a stain present in a polymeric matrix at a first concentration; a second slide having a second coating disposed on at least a portion of an upper surface of the second slide, the second coating comprising the stain present in the polymeric matrix at a second concentration; wherein the first concentration and the second concentration are different. In some embodiments, the stain is a chromogenic precipitate. In some embodiments, the chromogenic precipitate is derived from one of 5-Bromo-4-Chloro-3-Indolyl Phosphate; 4-Chloro-2-methyl benzenediazonium; 3,3'-Diaminobenzidine; 3,3',5,5;-tetramethylbenzidine; 4-chloro-1-naphthol; 2,2'-azino-bis(3-ethylbenzothiazoline-6-sulphonic acid); o-phenylenediamine dihydrochloride; p-Nitrophenyl Phosphate; 5-Bromo-4-Chloro-3-indolyl-B-D-Galactopyranoside; or 2,2,5-5-tetra-p-nitrophenyl-3,3-(3,3-dimethoxy-4,4-biphenylene)-di tetrazolium chloride. In some embodiments, the second concentration is at least twice the first concentration.

In another aspect of the present disclosure is a kit comprising: a first set of coating reagents comprising: a first intermediate coating solution comprising a first matrix forming component and an enzyme; and a second intermediate coating solution comprising a chromogen, wherein the chromogen is present in the second intermediate coating solution at a first concentration; and a second set of coating reagents comprising: a third intermediate coating solution comprising the first matrix forming component and the enzyme; and a fourth intermediate coating solution comprising the chromogen, wherein the chromogen is present in the fourth intermediate coating solution at a second concentration. In some embodiments, the kit further comprises a fifth intermediate coating solution comprising a crosslinking reagent. In some embodiments, the chromogen is selected from the group consisting of 5-Bromo-4-Chloro-3-Indolyl Phosphate; 4-Chloro-2-methyl benzenediazonium; 3,3'-Diaminobenzidine; 3,3',5,5;-tetramethylbenzidine; 4-chloro-1-naphthol; 2,2'-azino-bis(3-ethylbenzothiazoline-6-sulphonic acid); o-phenylenediamine dihydrochloride; p-Nitrophenyl Phosphate; 5-Bromo-4-Chloro-3-indolyl-B-D-Galactopyranoside; and 2,2,5-5-tetra-p-nitrophenyl-3,3-(3,3-dimethoxy-4,4-biphenylene)-di tetrazolium chloride. In some embodiments, the chromogen is 3,3'-Diaminobenzidine. In some embodiments, the enzyme is selected from the group consisting of alkaline phosphatase, horse radish peroxidase, glycosylases, and glucose oxidase. In some embodiments, the kit further comprises a plurality of optically transparent substrates.

BRIEF DESCRIPTION OF THE FIGURES

For a general understanding of the features of the disclosure, reference is made to the drawings. In the drawings, like reference numerals have been used throughout to identify identical elements.

FIG. 6 provides a side view of a substrate including a coating composition deposited onto an upper surface in accordance with some embodiments.

FIG. 8 provides a side view of a substrate including a medium defining a plurality of wells, whereby a coating composition is deposited into each well in accordance with some embodiments.

DETAILED DESCRIPTION

Figure 1:
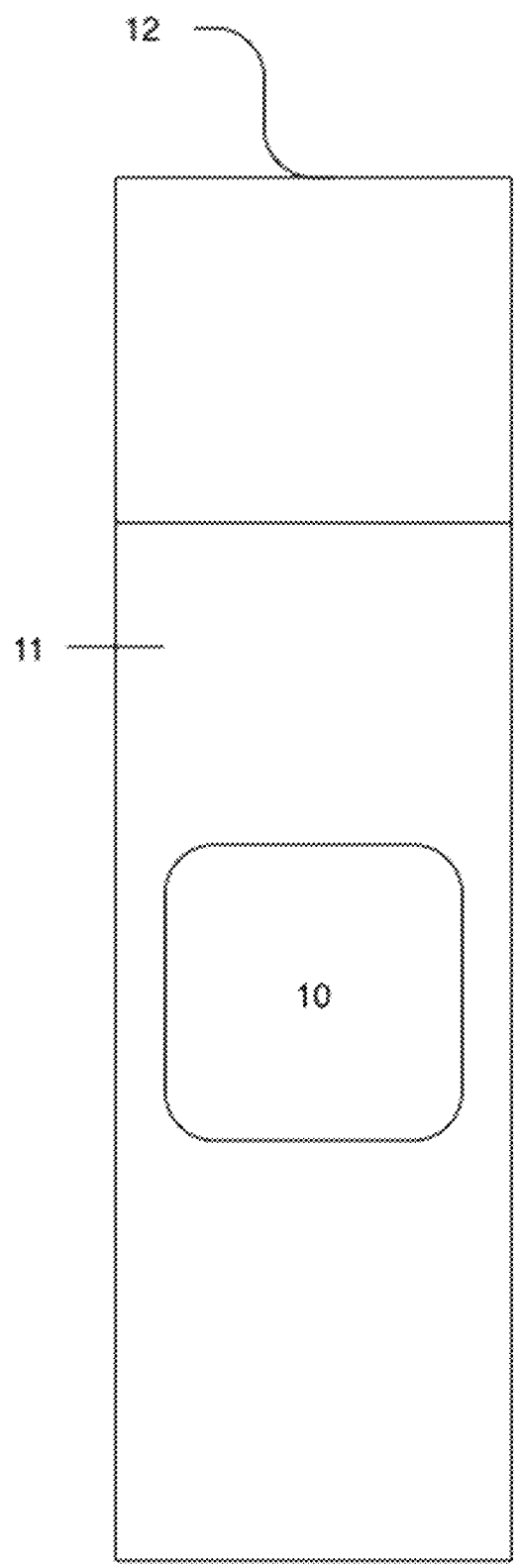
FIG. 1 depicts a coating composition deposited onto an upper surface of an optically transparent substrate in accordance with some embodiments.

It should also be understood that, unless clearly indicated to the contrary, in any methods claimed herein that include more than one step or act, the order of the steps or acts of the method is not necessarily limited to the order in which the steps or acts of the method are recited.

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of" or "exactly one of." "Consisting essentially of," when used in the claims, shall have its ordinary meaning as used in the field of patent law.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, the term "biological sample," "tissue sample," "specimen" or the like refers to any sample including a biomolecule (such as a protein, a peptide, a nucleic acid, a lipid, a carbohydrate, or a combination thereof) that is obtained from any organism including viruses. Other examples of organisms include mammals (such as humans; veterinary animals like cats, dogs, horses, cattle, and swine; and laboratory animals like mice, rats and primates), insects, annelids, arachnids, marsupials, reptiles, amphibians, bacteria, and fungi. Biological samples include tissue samples (such as tissue sections and needle biopsies of tissue), cell samples (such as cytological smears such as Pap smears or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, cerumen, milk, vaginal fluid, saliva, swabs (such as buccal swabs), or any material containing biomolecules that is derived from a first biological sample. In certain embodiments, the term "biological sample" as used herein refers to a sample (such as a homogenized or liquefied sample) prepared from a tumor or a portion thereof obtained from a subject.

As used herein, the term "biomarker" refers to a biological molecule found in blood, other body fluids, or tissues that is a sign of a normal or abnormal process, or of a condition or disease (such as cancer). A biomarker may be used to determine how well the body responds to a treatment for a disease or condition or if the subject is predisposed to a disease or condition. In the context of cancer, a biomarker refers to a biological substance that is indicative of the presence of cancer in the body. A biomarker may be a molecule secreted by a tumor or a specific response of the body to the presence of cancer. Genetic, epigenetic, proteomic, glycomic, and imaging biomarkers can be used for cancer diagnosis, prognosis, and epidemiology. Such biomarkers can be assayed in minimally invasive collected biofluids like blood or serum. Several gene and protein based biomarkers have already been used in patient care including but, not limited to, AFP (Liver Cancer), BCR-ABL (Chronic Myeloid Leukemia), BRCA1/BRCA2 (Breast/Ovarian Cancer), BRAF V600E (Melanoma/Colorectal Cancer), CA-125 (Ovarian Cancer), CA19.9 (Pancreatic Cancer), CEA (Colorectal Cancer), EGFR (Non-small-cell lung carcinoma), HER-2 (Breast Cancer), KIT (Gastrointestinal stromal tumor), PSA (Prostate Specific Antigen), S100 (Melanoma), and many others. Biomarkers may be useful as diagnostics (to identify early stage cancers) and/or prognostics (to forecast how aggressive a cancer is and/or predict how a subject will respond to a particular treatment and/or how likely a cancer is to recur).

As used herein, the term "chromogen" refers to a substance capable of conversion to and/or deposition of a colored product, such as a pigment or dye. Certain chromogens are electron donors that, when oxidized, become a colored product. Production of a colored product, and/or the property of becoming insoluble upon chemical conversion, such as by oxidation, make chromogens useful for IHC. Particular examples of chromogenic compounds, without limitation, include 3,3'-diaminobenzidine (DAB), tetramethylbenzidine (TMB), 2,2'-azino-di-[3-ethylbenzothiazoline sulphonate] (ABTS), iodonitrotetrazolium (INT), tetrazolium blue and tetrazolium violet. DAB is a chromogen that produces a brown end product (e.g. through an enzymatic reaction, such as HRP) that is highly insoluble in aqueous solutions.

As used herein, the term "concentration dependent stain" refers to a stain that does not strictly adhere to the Beer-Lambert law (which assumes small stain concentrations and no interaction between the absorbing molecules). For these concentration dependent stains, as the concentration of the stain increases, the proportions of R, G, B, channel signals changes in the detected light change due to increased scattering (such as caused by precipitation of stain molecules). For these types of stains, different optical density color reference vectors (determined at a plurality of varying stain concentrations) are utilized to best characterize the concentration-dependent nature of the stains, i.e. different color reference vectors determined at varying stain concentrations should be considered when selecting a color reference vector such that the effects of stain concentration are accounted for in the contributions of each of the R, G, and B channel signals in detected light.

As used herein, the term "hydrogel" refers to a macromolecular polymer gel constructed of a network of cross-linked polymer chains. They are synthesized from hydrophilic monomers by either chain or step growth, along with a functional crosslinker to promote network formation. Synthetic or natural polymers, homopolymer or copolymer, are used to make three dimensional networks by molecular entanglements or by chemical crosslinking As used herein, the term "substantially" means the qualitative condition of exhibiting total or near-total extent or degree of a characteristic or property of interest. In some embodiments, "substantially" means within about 20%. In some embodiments, "substantially" means within about 15%. In some embodiments, "substantially" means within about 10%. In some embodiments, "substantially" means within about 5%.

Overview

In some embodiments, histochemical staining is used to enhance the visual contrast of cell and tissue samples and highlight specific antigens present within cells. This is commonly achieved by embedding absorbing dyes into the sample material. To highlight multiple specific cell and tissue structures within a sample, multiple stains with different spectral absorption characteristics are deployed (i.e. multiplexing). Unfortunately, some of the most commonly used dyes, such as 3,3'-diaminobenzidine (DAB), Fast Red, and hematoxylin, are broadly absorbing. For example, broadly absorbing dyes have overlapping spectra which complicate color unmixing and quantification of the component dyes in the spectral properties of an acquired image or a pixel within the acquired image. This presents challenges when attempting to interpret the diagnostic information provided by the contrast of individual stains. Reconstruction of the single stain contrast from a multiplexed sample is highly desired.

In some embodiments, the present disclosure is directed to coatings or thin films comprising a dye or stain embedded within a matrix, e.g. a polymer matrix. In some embodiments, the coatings including the dye or stain may be deposited onto the surface of a substrate (e.g. an optically transparent substrate), such that the coated substrate may be used in a calibration procedure. For example, a coating comprising a stain may be deposited onto the surface of an optically transparent microscope slide to provide a calibration slide, the calibration slide suitable for calibrating a microscope or other scanning device. In some embodiments, multiple calibration slides (e.g. a set of calibration slides) may be used for calibration of a microscope or other slide scanning device, where each calibration slide includes a coating or thin film having the same dye or stain, but where the dye or stain is present in a different, known concentration. These and other aspects of the disclosure are described herein.

Coatings

In some aspects of the present disclosure are coatings or thin films comprising: (i) a matrix; and (ii) at least a dye or stain embedded or dispersed within the matrix. In some embodiments, the dye or stain is substantially uniformly embedded or dispersed within the matrix. In some embodiments, the dye or stain is a primary stain, e.g. hematoxylin or eosin. In some embodiments, the dye or stain is a chromogen. In other embodiments, the dye or stain is derived from a chromogen (e.g. a precipitate formed after an enzyme acts upon chromogen, the chromogen comprising at least a portion which is a substrate for the enzyme).

Non-limiting examples of chromogens which may be included within any coating or thin film include, but are not limited to, 5-Bromo-4-Chloro-3-Indolyl Phosphate (BCIP); 4-Chloro-2-methyl benzenediazonium (Fast Red TR); 3,3'-Diaminobenzidine (DAB); 3,3',5,5,;-tetramethylbenzidine (TMB); 4-chloro-1-naphthol (CN); 2,2'-azino-bis(3-ethylbenzothiazoline-6-sulphonic acid) (ABTS); o-phenylenediamine dihydrochloride (OPD); p-Nitrophenyl Phosphate (PNPP); 5-Bromo-4-Chloro-3-indolyl-B-D-Galactopyranoside (X-Gal); and 2,2,5-5-tetra-p-nitrophenyl-3,3-(3,3-dimethoxy-4,4-biphenylene)-ditetrazolium chloride (t-NBT). In some embodiments, the chromogens include at least a portion which is a substrate for an enzyme, such as an enzyme selected from the group consisting of alkaline phosphatase, horseradish peroxidase, glycosylases, and glucose oxidase. In some embodiments, DAB, which is oxidized in the presence of a peroxidase and hydrogen peroxide, results in the deposition of a brown, alcohol-insoluble precipitate at the site of enzymatic activity.

Additional non-limiting examples of chromogens which may be included within any coating or thin film include, but are not limited to, 4-nitrophenylphospate (pNPP), nitro blue tetrazolium (NBT), BCIP/NBT, AP Orange, AP blue, nitrophenyl-β-D-galactopyranoside (ONPG), 5methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, tetrazolium violet, N,N'-biscarboxypentyl-5,5'-disulfonato-indodicarbocyanine (Cy5), 4-(dimethylamino) azobenzene-4'-sulfonamide (DABSYL), tetramethylrhodamine (DISCO Purple), and Rhodamine 110 (Rhodamine).

Examples of enzymes and their chromogenic substrates include, but are not limited to, the following:
  McOSuc-AAPV-pNA, a substrate for neutrophil elastase;
  4-Methylumbelliferyl beta-D-glucuronide, a substrate for beta-glucuronidase;
  S-Butyrylthiocholine Iodide, a substrate for cholinesterases;
  Ac-DEVD-pNA, a substrate for caspase-3 (CPP32) and related cysteine proteases;
  4-Nitrophenyl alpha-D-galactopyranoside, a chromogenic substrate used to detect hydrolase enzymes;
  N-alpha-Benzoyl-L-arginine 4-nitroanilide hydrochloride, a chromogenic substrate for proteolytic enzymes;

4-Nitrophenyl-alpha-D-glucopyranoside, a chromogenic substrate for α-D-glucosidase;
GP-pNA, a chromogenic substrate for dipeptidyl peptidase IV;
Phenyl-beta-D-glucuronide, a β-glucuronidase substrate;
Ac-VAD-pNA, a substrate of caspase-1;
Nalpha-Benzoyl-DL-arginine beta-naphthylamide hydrochloride, a chromogenic substrate for trypsin;
Leu-pNA, an aminopeptidase substrate used to detect/evaluate functionality of aminopeptidases;
4-Nitrocatechol sulfate dipotassium salt, a chromogenic substrate for sulphatase;
4-Nitrophenyl alpha-L-rhamnopyranoside, a chromogenic substrate for naringinase;
Acetyl-DL-phenylalanine beta-naphthyl ester, a chromogenic substrate for chymotrypsin;
2-Methoxy-4-(2-nitrovinyl)phenyl beta-D-galactopyranoside, a 0-galactosidase chromogenic substrate;
4-Methylumbelliferyl beta-D-Cellotrioside, a chromogenic substrate for β-glycosidases;
Naphthol AS-MX phosphate disodium salt, a substrate for the histochemical demonstration of acid and alkaline phosphatase;
Chlorophenol Red-beta-D-galactopyranoside, a substrate for B-galactosidase;
RH 421, a chromogenic substrate for β-galactosidase;
6-Chloro-3-indolyl-beta-D-glucuronide cyclohexylammonium salt, a chromogenic substrate for β-glucuronidase;
Ac-VDVAD-pNA, a substrate for caspase-6;
1-Methyl-3-indolyl-beta-D-galactopyranoside, a chromogenic substrate for β-galactosidase;
5-Bromo-4-chloro-3-indoxyl palmitate, a chromogenic substrate for carboxylesterase;
4-Nitrophenyl thymidine-5prime-monophosphate, ammonium salt, a chromogenic substrate for Phosphodiesterase 1;
5-Bromo-6-chloro-3-indolyl beta-D-glucuronide cyclohexylammonium salt, a chromogenic substrate for β-glucuronidase;
NGB, a substrate for arginase;
4-Nitrophenyl alpha-D-xylopyranoside, a chromogenic substrate for α-xylosidase;
2-Methoxy-4-(2-nitrovinyl)phenyl beta-D-glucopyranoside, a chromogenic substrate for β-glucosidase;
p-Nitrophenyl 2-O-(beta-L-Fucopyranosyl)-beta-D-galactopyranoside, a chromogenic substrate used in the assay of α-fucosidases;
H-L-Pro-pNA Trifluoracetate, a colorimetric substrate for prolyl aminopeptidase; and
Indoxyl beta-D-galactopyranoside, a chromogenic β-galactosidase substrate.

In some embodiments, the dye or stain is a concentration dependent stain. In some embodiments, color reference vectors for concentration-dependent stains are derived by analyzing standardized samples at varying stain concentrations. For example, 3,3'-Diaminobenzidine ("DAB") is susceptible to the formation of precipitates, which causes light scattering, i.e. absorption in addition to scattering, and thus is a concentration-dependent stain. Likewise, Fast Red and AP Blue form precipitates, and are thus also concentration-dependent stains. The effect of the concentration of the DAB stain is further illustrated in Example 1 herein. As a result of the concentration-dependent nature of DAB, different color reference vectors should be considered when unmixing DAB. By way of example, rather than have a single color reference vector describing DAB, a plurality of different color reference vectors may be obtained for DAB, with each individual color reference vector of the plurality of different color reference vectors describing DAB at a particular concentration level (e.g. 1×, 5×, 10×, 15×, and 20×).

As noted above, the dye or stain is embedded or dispersed within a matrix, such as substantially uniformly embedded or dispersed within the matrix. In some embodiments, the matrix is a hydrogel. In some embodiments, chemical or permanent hydrogels are formed by covalent crosslinking of polymers. Hydrogels may be crosslinked with many compounds, including aldehydes, such as glutaraldehyde. In some embodiments, the hydrogel is generated by crosslinking a gelling agent with a crosslinking agent, e.g. glutaraldehyde. In some embodiments, the gelling agent is a colloid such as tragacanth, acacia, agarose, agar-agar, dextrin, or gelatin. Other crosslinking compounds include formaldehyde, epoxy compounds, and dialdehyde. The strength of hydrogels can be increased by incorporating additional crosslinking agents, comonomers, and/or increasing the degree of crosslinking.

In some embodiments, the hydrogel matrix material may be derived from albumin. Albumin containing matrices may comprise a serum albumin conjugated with a cross-linking agent. The cross-linking agent may be selected from the group consisting of glutaraldehyde, amino acids, polypeptides and proteins.

In some embodiments, the hydrogels are polysaccharide hydrogels. Polysaccharide hydrogels can be formed by covalent crosslinking, chemical conjugation, esterification and polymerization. Examples of polysaccharides suitable for use in forming hydrogels include, but are not limited to, chitosan, hyaluronic acid, the family of chondroitin sulfates, heparin, keratan sulfate, glycogen, glucose, amylase, amylopectin and derivatives thereof. The polysaccharide may be naturally occurring or synthetically produced. Polysaccharides have several reactive groups that are available for chemical modification. These include the hydroxyl (OH), carboxyl (COOH), and acetamido ($COCH_3$) groups. Further functionality can be imparted to specific polysaccharides in the form of an amine ($NH_2$) group via basic deacetylation, in which a polysaccharide is exposed to basic conditions at elevated temperatures. In some embodiments, the polysaccharide (e.g., chitosan) is present in a salt or amine form. In some embodiments, the polysaccharide is chitosan. In some embodiments, the chitosan may have a molecular weight in the range of 10 Dalton to 1 kD; the range of 1 kD to 10 kD; the range of 10 kD to 100 kD; the range of 100 kD to 250 kD; the range of 250 kD to 500 kD; or the range of 500 kD to 1000 kD.

In addition, polysaccharides may be combined with proteins such as collagen, gelatin, laminin and fibrin to form an interpenetrating network or composite hydrogels. In some embodiments, the polysaccharide hydrogels may further include a hydrophilic polymer such as any of the following natural, synthetic, or hybrid polymers: poly(ethylene glycol), poly(ethylene oxide), poly(vinyl alcohol), poly(allyl alcohol), poly(vinylpyrrolidone), poly(alkylene oxides), poly(oxyethylated polyols), poly(ethyleneimine), poly(allylamine), poly(vinyl amine), poly(aminoacids), poly(ethyloxazoline), poly(ethylene oxide)-co-poly(propylene oxide) block copolymers, polysaccharides, carbohydrates, oligopeptides, and polypeptides.

Protein-based hydrogels can be formed by thermal gelation and their mechanical properties can be enhanced using chemical crosslinkers such as glutaraldehyde. Examples of protein-based hydrogels include those formed from albumin, fibrin, protein-lipid combinations (e.g. myelin), gelatin, elastin, and isinglass.

In some embodiments, the hydrogel is prepared from various vinylated monomers or macromers, such as 2-hydroxyethyl methacrylate (HEMA), 2-hydroxypropyl methacrylate (HPMA), acrylamide (AAm), acrylic acid (AAc), N-isopropylacrylamide (NIPAm), and methoxyl poly (ethylene glycol) (PEG) monoacrylate (mPEGMA or PEGMA), with crosslinkers, such as N,N-methylenebis(acrylamide) (MBA), ethylene glycol diacrylate (EGDA) and PEG diacrylate (PEGDA). PEG-based hydrogels can be prepared by radiation crosslinking of PEG or free radical polymerization of PEG macromers.

Further examples of polymers which may be used to form a hydrogel include, but are not limited to: poly(propylene oxide) (PPO), poly(butylene oxide) (PBO), poly(2-hydroxyethyl methacrylate), hydroxyethyl methacrylate, poly(ethylene glycol) methacrylate, acrylic acid acrylamide, N-isopropylacrylamide, poly(vinyl alcohol) (PVA), polyacrylamide (PAAm), poly(N-vinyl pyrrolidone) (PNVP), poly(hydroxyethyl methacrylate) PHEMA), poly(ethylene oxide) (PEO), poly(ethylene glycol) monomethyl ether (PEGME), methyl cellulose such as carboxymethyl cellulose, poly(hydroxyethyl methacrylate) (PHEMA) copolymerized with NVP methacrylic acid (MAA), butyl methacrylate (BMA), methyl methacrylate (MMA), 3-methoxy-2-hydroxypropylmethacrylate (MI IPM), PHEMA/poly(ethyleneterephthalate) (PTFE), PHEMA, P(HEMA-co-MMA), P(HEMA-b-siloxane), PVA, poly(acrylic acid) (PAA), poly (gliceriyl methacrylate), HEMA, polycyanoacrylates, fumaric acid-PEG, sebacic acid/1,3-bis(p-carboxyphenoxy) propane (P(CPP-SA)) PHEMA, PVA, PNVP, poly(ethylene-co-vinyl acetate) (PEVAc), poly(acrylamide) (PAAm), poly (diethylaminoethyl methacrylate) (PDEAEMA), poly (dimethylaminoethyl methacrylate), (PDMAEMA), poly(methacrylic acid-grafted-poly(ethylene glycol)), (P(MAA-g-EG)), poly (acrylic acid-grafted-poly(ethylene glycol) (P(PAA-g-EG)), poly(N-isopropyl acrylamide) (PNIPAAm), PNIPAAm/PAA, polyglycol-alginate, collagen based gels (gelatins), and heparan sulfate and its analogues and other glycosaminoglycans.

In some embodiments, the hydrogel is a silicon hydrogel. Suitable hydrogels include copolymers of (i) one or more hydrophilic monomers, for example selected from the group of hydroxyethylacrylate, hydroxyethylmethacrylate, acrylamide, N,N-dimethyl acrylamide, a vinyl lactame such as N-vinylpyrrolidone, a (meth)acryloyloxyethyl phosphorylcholine, such as 2-acryloyloxyethyl phosphorylcholine or 2-methacryloyloxyethyl-'-(trimethylammonium)ethyl phosphoryl-choline, N-vinyloxycarbonyl-L-alanine, acrylic or methacrylic acid; and (ii) a monomer and/or macromonomer comprising a siloxane bond or silane group, e.g. trimethylsilyl group.

In some embodiments, thickening agents may be added to the hydrogel compositions. The thickening agents include, for example, dextran, carboxymethyl cellulose, polyethylene glycol, liposomes, proliposomes, glycerol, starch, carbohydrates, povidone, polyethylene oxide, and polyvinyl alcohol. In some embodiments, the thickening agent is dextran, polyethylene glycol or carboxymethyl cellulose. In some embodiments, any hydrogel composition may comprise at least about 1% thickening agent by total weight of the hydrogel concentration (or the matrix formed from the hydrogel). In other embodiments, any hydrogel composition may comprise at least about 5% thickening agent by total weight of the hydrogel concentration (or the matrix formed from the hydrogel). In yet other embodiments, any hydrogel composition may comprise at least about 10% thickening agent by total weight of the hydrogel concentration (or the matrix formed from the hydrogel).

In some embodiments, the matrix may optionally include a variety of naturally occurring or synthetically produced additives such as, but not limited to, water, buffer, saline solution, neutral salt, carbohydrate, fiber, miscellaneous biological material, wetting agent, antibiotics, preservative, dye, thickening agent, thinning agent, fibrinogen, polymer such as polyethylene glycol or combination thereof.

In some embodiments, the matrix comprises a polymer. Polymers include synthetic polymers such as, polyamides, polyesters, polystyrenes, polyacrylates, vinyl polymers (e.g., polyethylene, polytetrafluoro-ethylene, polypropylene and polyvinyl chloride), polycarbonates, polyurethanes, poly dimethyl siloxanes, cellulose acetates, polymethyl methacrylates, acrylamides, ethylene vinyl acetates, polysulfones, nitrocelluloses and similar copolymers. Biological polymers include, without limitation, collagen, elastin, silk, keratin, gelatin, polyamino acids, polysaccharides (e.g., cellulose and starch) and copolymers thereof.

Other suitable polymers include polysiloxanes, perfluoroalkyl polyethers, fluorinated poly(meth)acrylates, polyalkyl (meth)acrylates, or fluorinated polyolefines, such as fluorinated ethylene or propylene, for example tetrafluoroethylene. Yet other suitable polymers include polyolefins, polyolefin copolymers, polyesters, and polyamines. Yet further examples of suitable polymers include poly(styrene sulfonate, sodium salt), poly(styrene sulfonic acid), poly (styrene sulfonic acid/maleic anhydride), poly(2-acrylamido-2-methyl-propane sulfonic acid/acrylic acid/methyl acrylate/benzyl methacrylate/ETEGMA), poly(styrene/dimethylamino ethylmethacrylate/hydroxyethylacrylate), poly (benzyl methacrylate/hydroxyethyl acrylate), poly (benzyl methacrylate/dimethyl amino ethylmethacrylate).

Polymers of monoolefins and diolefins include, for example, polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight poly-ethylene (HDPE-UHMW), medium density polyethylene (MDPE), low density polyethylene (LDPE), linear low density polyethylene (LLDPE), (VLDPE) and (ULDPE).

Polyolefin copolymers include copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Examples of polyesters include those derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also, polyesters modified with polycarbonates or MBS. Preferred is polyethylene terephthalate (PET).

Examples of polyamines include those derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Yet other suitable matrix materials include gelatin and di-aldehyde starch as described in PCT WO 97/29715; 4-armed pentaerythritol tetra-thiol and polyethylene glycol diacrylate as described in PCT WO 00/44808; photo-polymerizable polyethylene glycol-co-poly(a-hydroxy acid) diacrylate macromers as described in U.S. Pat. No. 5,410,016; periodate-oxidized gelatin as described in U.S. Pat. No. 5,618,551; serum albumin and di-functional polyethylene glycol derivatized with maleimidyl, succinimidyl, phthalimidyl and related active groups as described in PCT WO 96/03159; whereby each of the aforementioned PCT Publications or United States granted patents are hereby incorporated by reference herein in their entireties.

Yet further suitable matrix materials include those derived from a copolymer of polyethylene glycol and polylactide, polyglycolide, polyhydroxybutyrates or polymers of aromatic organic amino acids and sometimes further containing acrylate side chains, gelled by light, in the presence of some activating molecules. Another type of the suitable matrix material is 4-armed polyethylene glycol derivatized with succinimidyl ester and thiol plus methylated collagen in two-part polymer compositions that rapidly form a matrix where at least one of the compounds is polymeric, such as polyamino acid, polysaccharide, polyalkylene oxide or polyethylene glycol and two parts are linked through a covalent bond, for example a cross-linked PEG with methyl collagen, such as a cross-linked polyethylene glycol hydrogel with methyl-collagen, as described in U.S. Pat. Nos. 6,312,725B1 and 6,624,245B2, the disclosures of which are hereby incorporated by reference herein in their entireties.

In other embodiments, a ratio of the chromogenic precipitate to the polymer ranges from about 0.1 to about 80. In yet other embodiments, a ratio of the chromogenic precipitate to the polymer ranges from about 0.1 to about 60. In further embodiments, a ratio of the chromogenic precipitate to the polymer ranges from about 0.1 to about 40. In yet further embodiments, a ratio of the chromogenic precipitate to the polymer ranges from about 0.1 to about 20. In other embodiments, a ratio of the chromogenic precipitate to the polymer ranges from about 0.1 to about 10. In yet other embodiments, a ratio of the chromogenic precipitate to the polymer ranges from about 0.1 to about 5. In yet other embodiments, a ratio of an amount of dye or stain to the matrix forming material ranges from about 0.15 to about 4. In other embodiments, a ratio of an amount of dye or stain to the matrix ranges from about 0.2 to about 4.

Substrates Including a Coating or Thin Film

The coatings either be applied to or formed directly on a substrate, such as an optically transparent substrate. In some embodiments, the substrate is a slide, a lens filter, and targets, including those that are contained within a holder, whereby the holder may be cuboid or cylindrical in shape. In other embodiments, the substrate is a slide. As used herein, the term "slide" refers to any substrate (e.g., substrates made, in whole or in part, glass, quartz, plastic, silicon, etc.) of any suitable dimensions on which a biological specimen is placed for analysis, and more particularly to a "microscope slide" such as a standard 3 inch by 1-inch microscope slide or a standard 75 mm by 25 mm microscope slide.

In some embodiments, the slide is optically transparent at a working wavelength, which allows transmitting light without appreciable scattering or absorption. In some embodiments, the slide is may be fully transparent. For example, the slide can transmit more than 90 percent of light. In some embodiments, the slide may also be partially transparent. For example, the slide is can transmit 60 percent of light.

In some embodiments, the coating deposited or formed on the substrate has a thickness ranging from between about 0.5 µm to about 1000 µm. In other embodiments, the coating deposited or formed on the substrate has a thickness ranging from between about 0.5 µm to about 500 µm. In yet other embodiments, the coating deposited or formed on the substrate has a thickness ranging from between about 0.5 µm to about 400 µm. In yet other embodiments, the coating deposited or formed on the substrate has a thickness ranging from between about 1 µm to about 300 µm. In yet other embodiments, the coating deposited or formed on the substrate has a thickness ranging from between about 0.5 µm to about 200 µm. In yet other embodiments, the coating deposited or formed on the substrate has a thickness ranging from between about 0.5 µm to about 10,000 µm. In some embodiments, the thickness of the film is substantially uniform. For example, the thickness of the film may vary by at most 5%. In other embodiments, the thickness of the film may vary by at most 2.5%.

In some embodiments, the coating is disposed on at least a portion of a microscope slide. As illustrated in FIG. 1, a coating 10 may be deposited or formed on an upper surface 11 of a microscope slide 12. As described above, a dye or stain is substantially uniformly distributed throughout coating 10, i.e. there exists a substantially uniform dye or stain concentration distributed throughout the coating 10. In some embodiments, a coverslip may be applied over any coating. In some embodiments, the coating 10 may be imaged with a scanner (e.g. the DP 200 Scanner, available from Ventana Medical Systems, Inc.) and color reference vectors may be derived for the coating.

Figure 2:
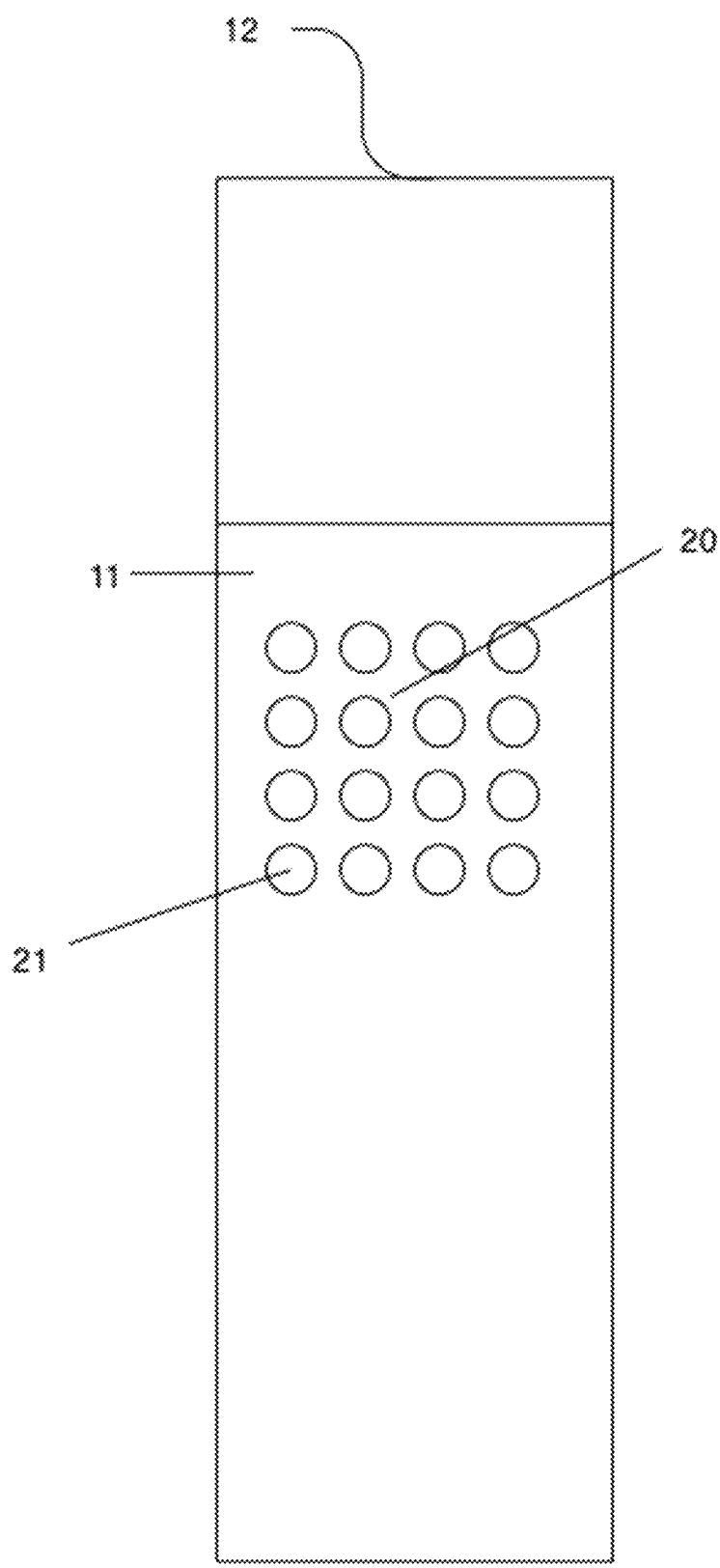
FIG. 2 depicts a coating array deposited onto an upper surface of an optically transparent substrate, the coating array comprising a plurality of coating array members in accordance with some embodiments.

In other embodiments, and as illustrated in FIG. 2, a coating array 20 may be deposited or formed on an upper surface 11 of a microslide slide 12, whereby the coating array 20 includes a plurality of array members 21. In some embodiments, a coating array may comprise at least two array members 21. In other embodiments, aa coating array may comprise from 2 to 30 array members 21. While the individual array members 21 are depicted in FIG. 2 as circles, the array members may have any size or shape (e.g. rectangles, circles, ovals, etc.). In some embodiments, each individual array member 21 includes the same coating components (i.e. the same dye or stain embedded within the same matrix forming material) and where each coating component is included in the same amount or concentration.

Figure 3A:
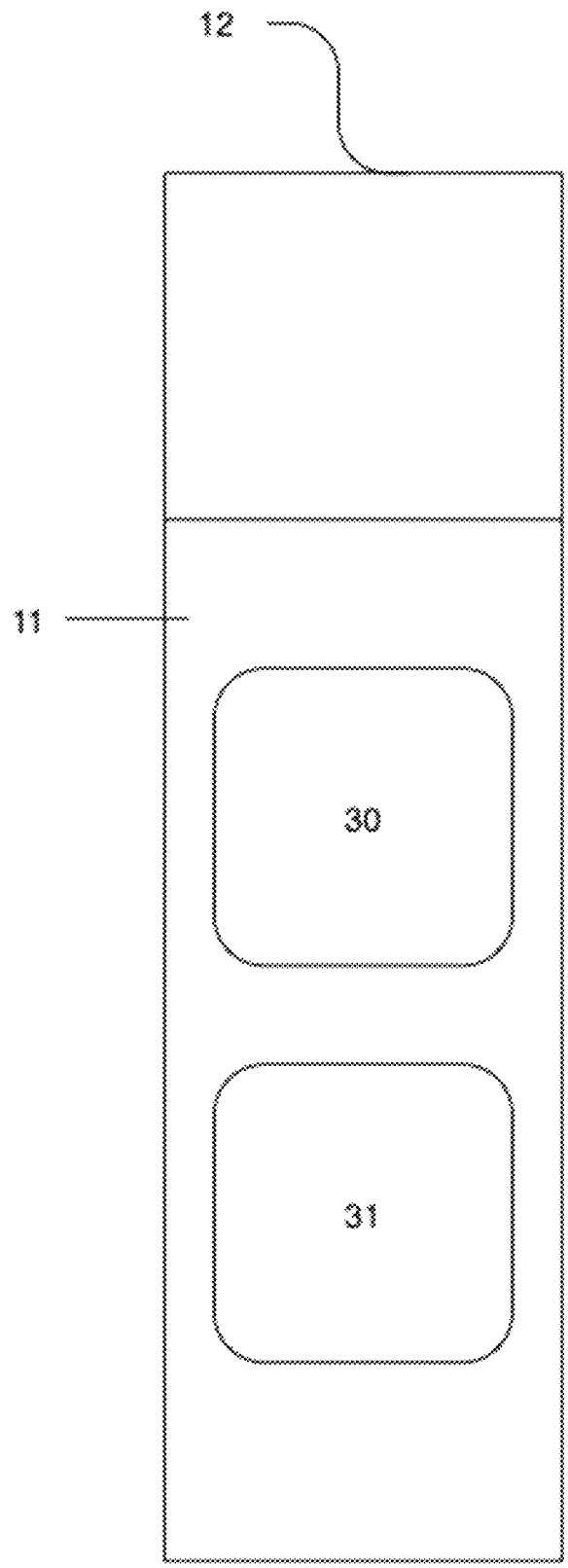
FIG. 3A depicts two coating compositions deposited adjacent to each other onto an upper surface of an optically transparent substrate in accordance with some embodiments.

In some embodiments, multiple different coatings or multiple different coating arrays may be present on an individual slide 12. For example, FIG. 3A illustrates a first coating 30 deposited or formed on an upper surface 11 of a microscope slide 12; and a second coating 31 deposited or formed proximal to the first coating 30. In some embodiments, the first coating 30 comprises different coating composition components as compared with the coating composition components in the second coating 31. In other embodiments, the first coating 30 comprises different amounts of coating composition components as compared with the amounts of coating components in the second coating 31 (i.e. the same composition components are included in the first and second coatings but at least one of those components in the second coating are present in a different amount as compared with the first coating). For example, the first coating 30 may comprise a precipitate of DAB at a first concentration in a hydrogel matrix while the second coating 31 may comprise a precipitate of DAB at a second concentration in the same hydrogel matrix.

Figure 3B:
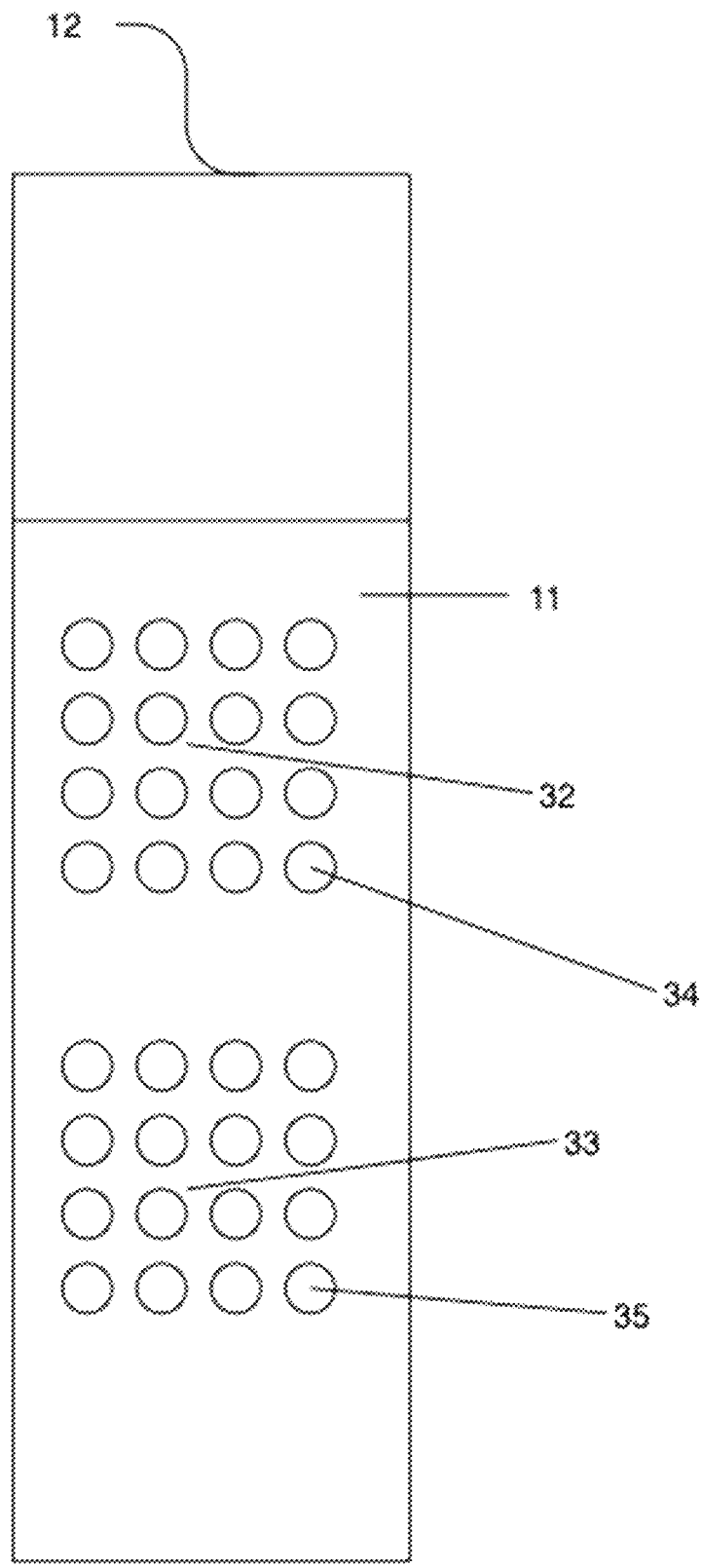
FIG. 3B depicts two coating arrays deposited adjacent to each other onto an upper surface of an optically transparent substrate in accordance with some embodiments.

Likewise, FIG. 3B illustrates a first coating array 32 deposited or formed on an upper surface 11 of a microscope slide 12; and a second coating array 33 deposited or formed proximal to the first coating array 32. In some embodiments, each individual first array member 34 of the first coating array 32 is the same as every other member in the first array (i.e. each array member comprises the same coating composition components in the same amounts). Similarly, each individual second array member 35 of the second coating array 33 is the same as every other member in the second array (i.e. comprises the same components in the same amounts). However, in some embodiments, the components or amounts of components in the first coating array 32 may differ from the components or amounts of components in the second coating array 33. For example, each of the array members of the first coating array 32 may comprise a precipitate derived from DAB at a first concentration in a hydrogel matrix (i.e. each individual array member 34 comprises a precipitate derived from DAB at the first concentration) while each of the array members of the second coating array 33 may comprise a precipitate of DAB at a second concentration in the same hydrogel matrix (i.e. each individual array member 35 comprises a precipitate of DAB at a second concentration). In some embodiments, the first coating array 32 and the second coating array 33 may be analyzed or imaged individually, such that color reference vectors may be separately derived for each coating array.

Figure 4:
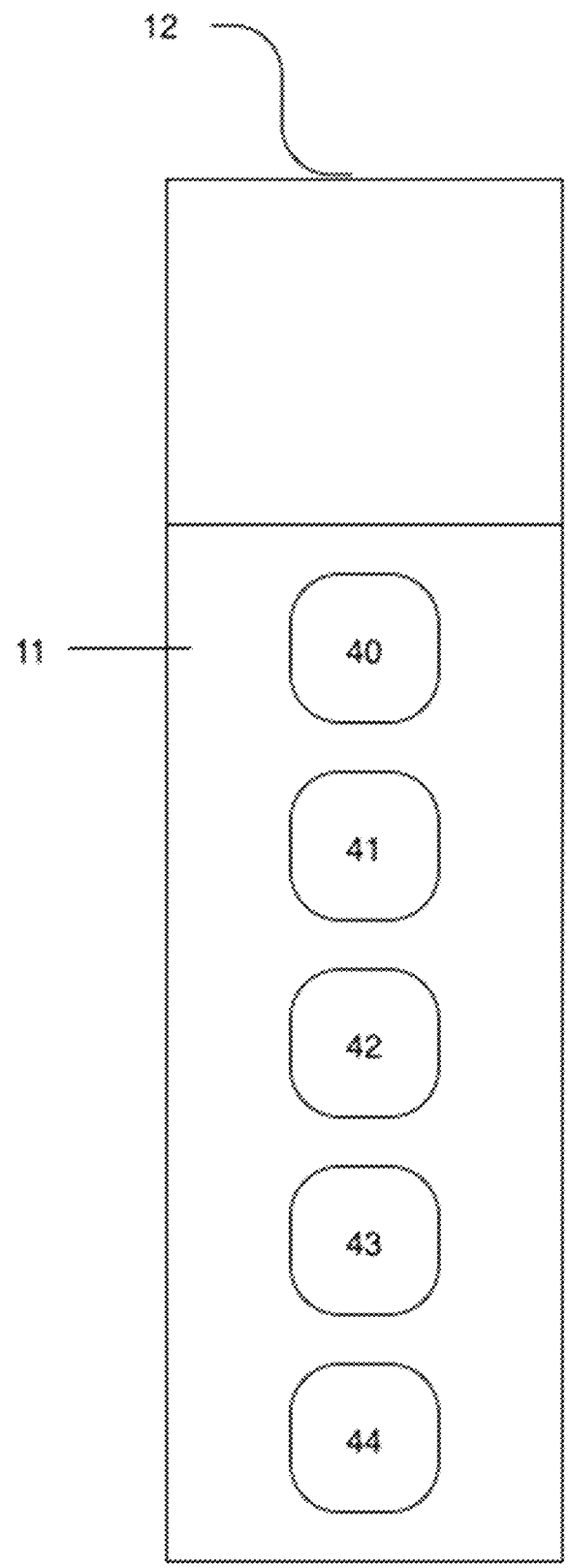
FIG. 4 depicts five coating compositions deposited adjacent to each other onto an upper surface of an optically transparent substrate in accordance with some embodiments.

In some embodiments, a single slide may comprise 3, 4, 5, or more coating areas or coating arrays. For example, FIG. 4 depicts a microscope slide 12 whereby five coating areas 40, 41, 42, 43, and 44 are deposited or form on an upper surface 11 of the slide 12. In some embodiments, the five coating areas 40, 41, 42, 43, and 44 comprise different concentrations of a dye or stain. For example, coating area 40 may comprise a 1× concentration of a stain; coating area 41 may comprise a 5× concentration of a stain; coating area 42 may comprise a 10× concentration of stain; coating area 43 may comprise a 15× concentration of stain; and coating area 44 may comprise a 20× concentration of stain. In some embodiments, each of the 3, 4, 5, or more coatings may be individually observed with a microscope or imaged with a scanner.

In some embodiments, a set of calibration slides may be prepared. In some embodiments, a set of calibration slides may include at least 3 calibration slides, where each calibration slide includes a dye or stain at a different concentration level. In other embodiments, a set of calibration slides may include at least 4 calibration slides, where each calibration slide includes a dye or stain at a different concentration level. In yet other embodiments, a set of calibration slides may include at least 5 calibration slides, where each calibration slide includes a dye or stain at a different concentration level. In some embodiments, a set of calibration slides can include from 2 to 20 different calibration slides, each different calibration slide including a dye or stain at a different concentration level.

Figure 5:
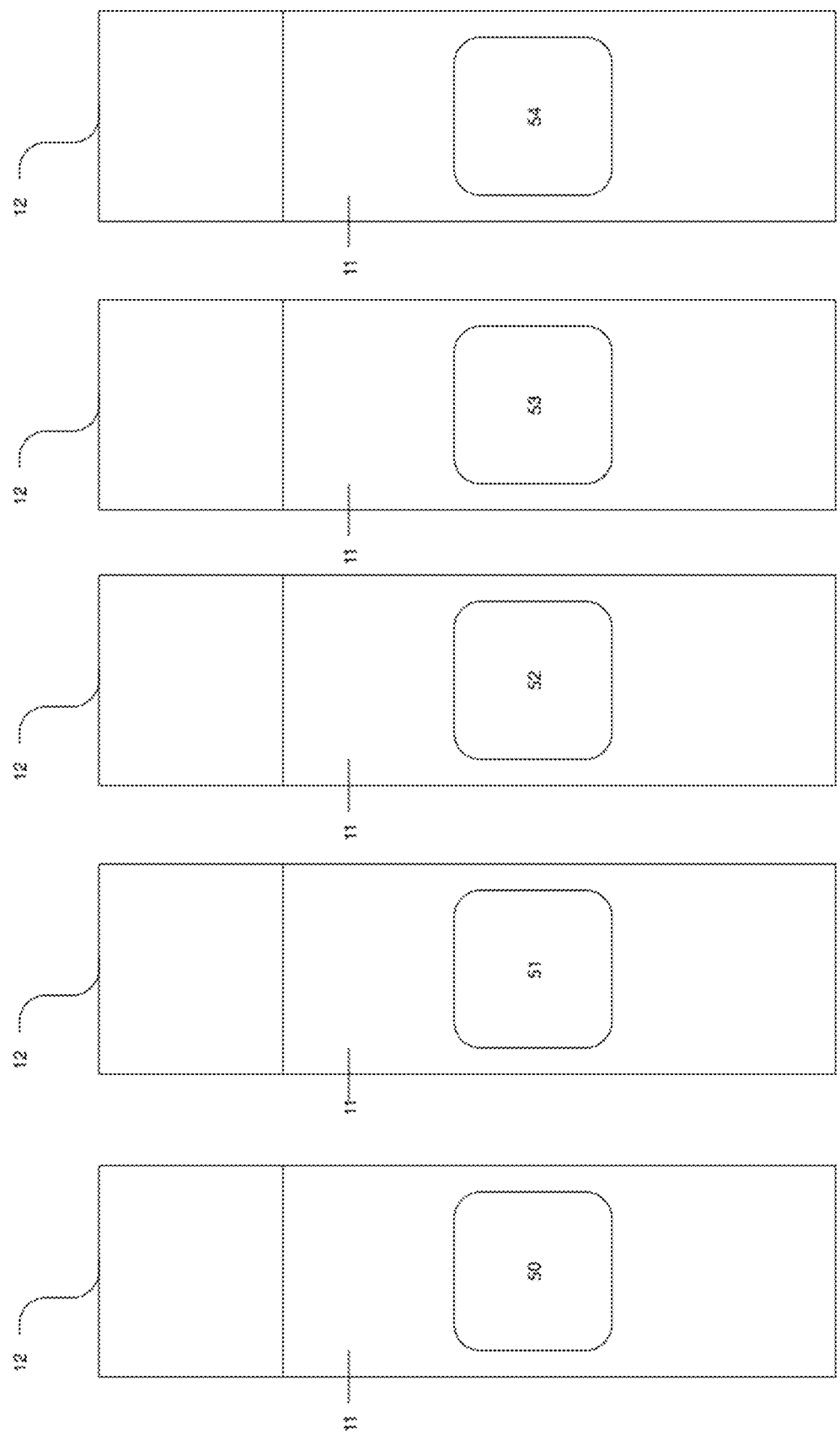
FIG. 5 depicts a set of five discrete substrates, each having a coating composition deposited thereon in accordance with some embodiments.

In some embodiments, each individual calibration slide of the set of calibration slides may include a coating having a dye or stain embedded or dispersed within a matrix. In some embodiments, each set of calibration slides will include a coating having the same dye or stain, except that a different concentration of dye or stain present will be present in each separate coating in the set. For example, and with reference to FIG. 5, a first slide may include a first coating 50 having a dye or stain present in a first concentration; a second slide may include a second coating 51 having the same dye or stain present in a second concentration; a third slide may include a third coating 52 having the same dye or stain present in a third concentration; a fourth slide may include a fourth coating 53 having the same dye or same present in a fourth concentration; and a fifth slide may include a fifth coating 54 having the same concentration or stain present in a fifth concentration. In this way, each slide may be separately scanned and color reference vectors may be separately derived for the dye or stain at five different dye or stain concentration levels, e.g. at a first concentration level, at a second concentration level that is 5× the first concentration level, at a fourth concentration level that is 10× the first concentration level, at a second concentration level that is 15× the first concentration level, and/or at a fifth concentration level that is 20× the first concentration level.

Figure 7A:
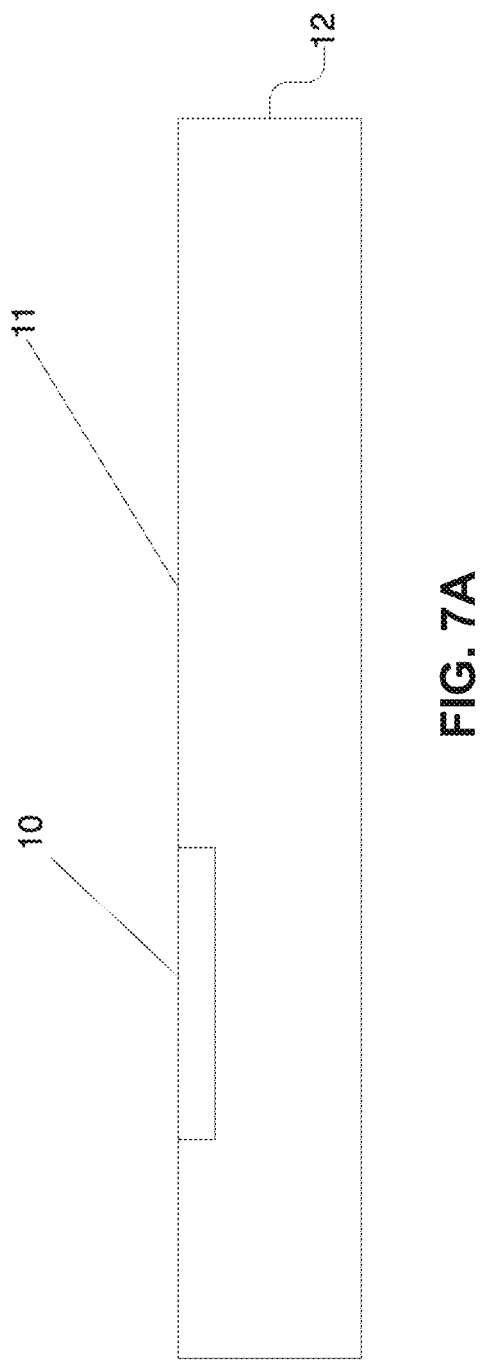
FIG. 7A provides a side view of a substrate having a well, the substrate including a coating composition deposited into the well in accordance with some embodiments.
Figure 7B:
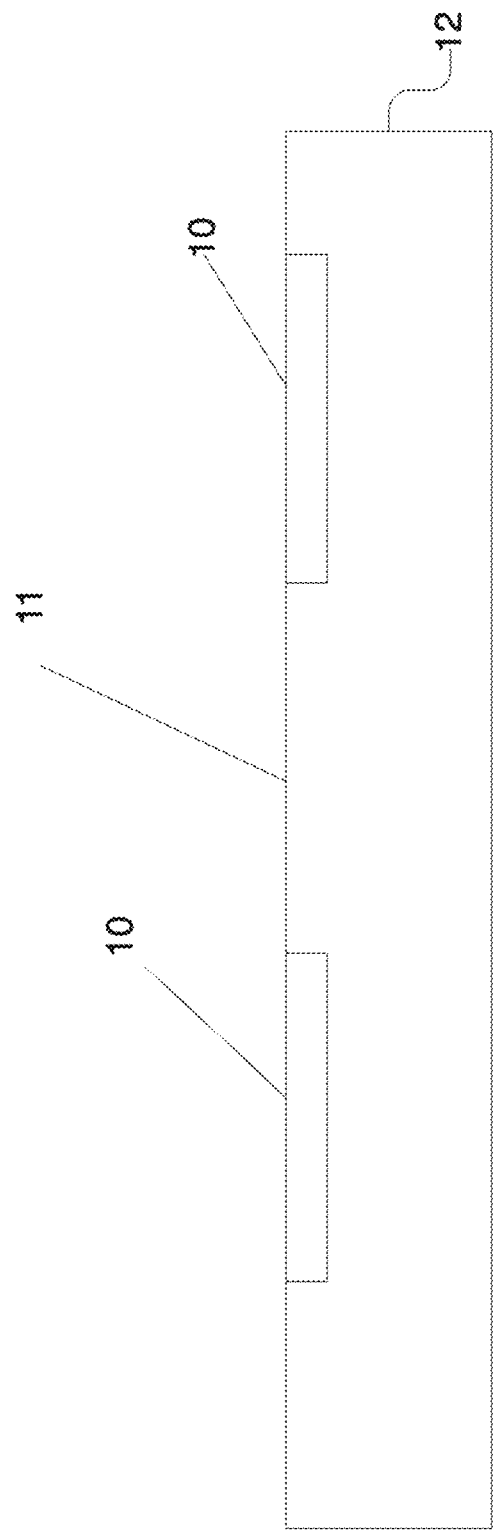
FIG. 7B provides a side view of a substrate having at least two wells, the substrate including a coating composition deposited into the well in accordance with some embodiments.

While FIGS. 1, 2, 3A, 3B, 4, and 5 depict a coating or coating array deposited on the surface of a substrate, the coating composition may be present within a well or other indented area of a substrate. For example, FIG. 6 illustrates a coating 10 deposited onto the surface 11 of substrate 12. Alternatively, the coating 10 can be deposited into a well within substrate 12, such as depicted in FIGS. 7A and 7B (FIG. 7A depicts a substrate having a single well, while FIG. 7B depicts a substrate having multiple wells). The skilled artisan will appreciate that any coating deposited into a well may have a thickness such that it is level with surface 11; or, may have a thickness whereby the coating is either above or below the surface 11. FIG. 8 depicts yet another alternative embodiment where by a medium 13 in communication with an upper surface 11 of substrate 12 comprises one or more wells or indentations, and whereby a coating composition 10 is deposited within the one or more wells or indentations of the medium 13.

Methods of Forming the Coated Substrates

The present disclosure also provides methods of making the coated substrates. In some embodiments, a coating may be prepared by depositing a coating solution onto the surface of a substrate, where the coating solution may be allowed to form a matrix. In some embodiments, the formation of the matrix may be via a passive step (e.g. cooling of a coating solution from an elevated temperature to room temperature, such that a polymeric matrix may form) or an active step (e.g. adding a crosslinking agent to the coating solution to enable crosslinking of a first matrix-forming component). For example, a coating solution comprising (i) a dye or stain; and (ii) a first constituent component of the matrix, may be prepared and then that coating solution may be deposited onto a surface of a substrate (or may be deposited into a well within the substrate or within a medium in communication with the substrate). Subsequently, a crosslinking agent may be added to the coating solution so as to crosslink the first constituent component of the matrix. By way of another example, a coating solution comprising a chromogen and gelatin may be synthesized. That coating solution may then be deposited onto the surface of the slide. Subsequently, a crosslinking agent, e.g. glutaraldehyde, may be added such that the gelatin becomes crosslinked, thereby forming the matrix including the dye or stain.

In some embodiments, the coating solution may comprise additional components, e.g. an enzyme such that a chromogenic precipitate may be generated. In some embodiments, the additional components are those typically introduced to a specimen during a staining process, e.g. the additional components are those typically introduced to a specimen when staining a sample for the presence of a particular biomarker. For example, in an immunohistochemical staining process, a sample may be contacted with an antibody specific for a particular target, the antibody being coupled to an enzyme. In this way, the target may become "labeled" with an enzyme. Following the labeling of the target with the enzyme, a substrate for the enzyme may be introduced (e.g. a chromogen) such that a precipitate may be deposited proximal to the target. It is this chromogenic precipitate that is ultimately detected (such as visually) such that the biomarker may be identified.

Figure 9:
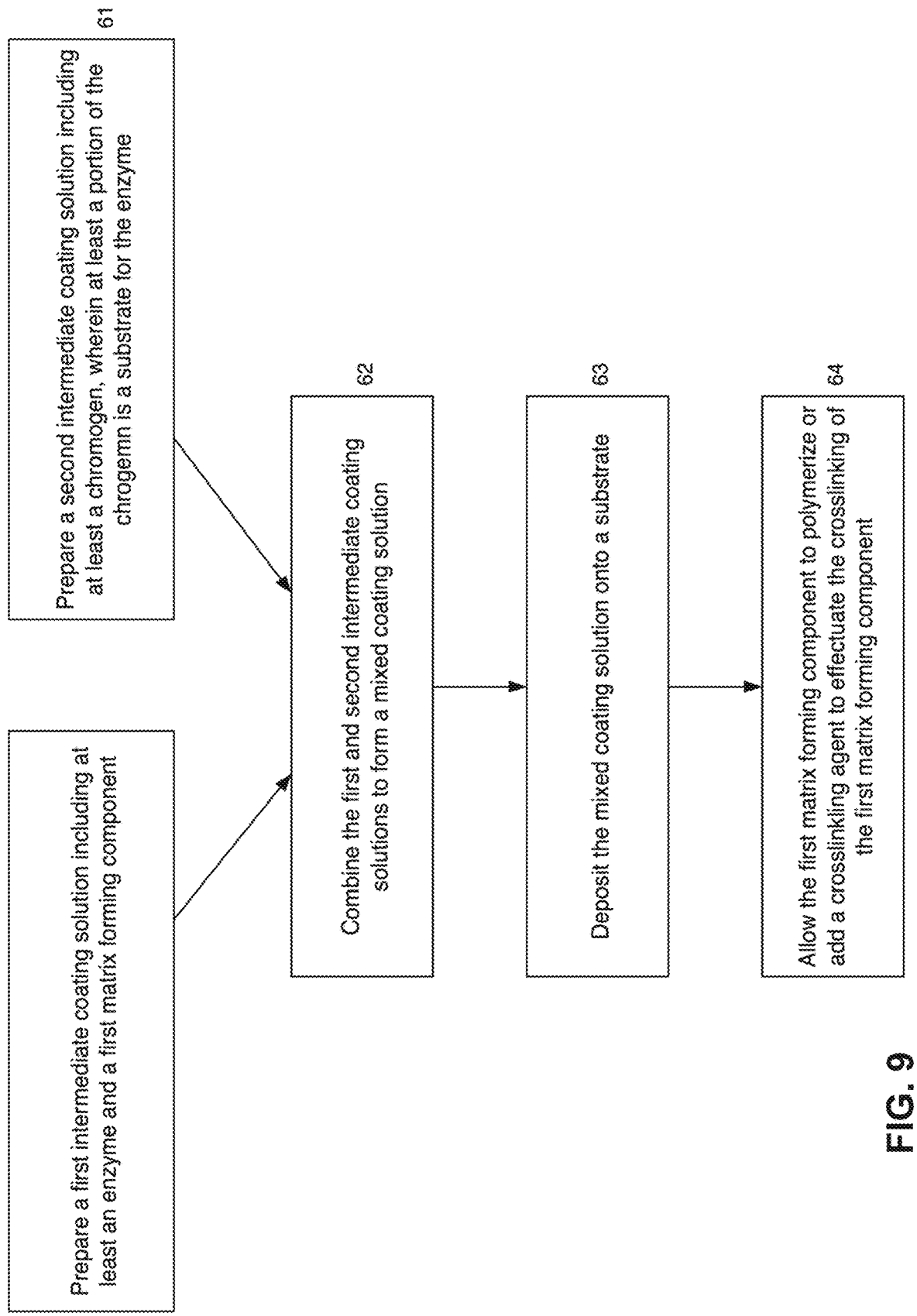
FIG. 9 sets forth a flowchart illustrating the steps of forming a mixed coating solution for deposition onto a substrate in accordance with some embodiments.

In some embodiments, to calibrate a microscope or scanning device for the chromogenic precipitate to be detected in any particular immunohistochemistry assay or in situ hybridization assay, it is sometimes necessary that a precipitate be formed in a coating solution just as it would be in an immunohistochemistry assay or in an in situ hybridization assay. As such, in some embodiments, an enzyme is included within any coating solution along with its substrate, such that a chromogenic precipitate is formed in situ within the coating solution. With reference to FIG. 9, in some embodiments, a first intermediate coating solution may be prepared including a first matrix forming component and an enzyme (step 60). In some embodiments, a second intermediate coating solution may be prepared including at least a chromogen, the chromogen being a substrate for the enzyme (step 61). In some embodiments, the first and second intermediate coating solutions are then combined to provide a mixed coating solution, the mixed coating solution including a generated chromogenic precipitate (step 62), i.e. the enzyme acts upon the chromogen to produce the chromogenic precipitate. The mixed coating solution may then be applied to a substrate (step 63), whereby the deposited mixed coating solution may form a matrix (e.g. polymerization of one or more monomers; the addition of a crosslinking agent). This process is further described in Example 2, herein. The skilled artisan will appreciate that steps 60 through 64 may be repeated any number of times to provide a plurality of different calibration slides, whereby each different calibration slide of the plurality of different calibration slides includes a different concentration of chromogen in the first intermediate coating solution.

Kits

The present disclosure also provides kits comprising a dye or stain and a matrix-forming component. In some embodiments, the present disclosure comprises a kit comprising a first intermediate coating solution and a second intermediate coating solution. In some embodiments, when the first and second intermediate coating solutions are mixed and deposited onto a substrate, a coating or thin film may be formed including a dye or stain embedded or dispersed within a matrix.

In some embodiments is a kit comprising a first intermediate coating solution comprising a dye or stain; and a second intermediate coating solution comprising at least one matrix forming component. In other embodiments is a kit comprising a first intermediate coating solution comprising a dye or stain and a first matrix forming component; and a second intermediate coating solution comprising a second matrix forming component. In some embodiments, the first matrix forming component is a material that is capable of crosslinking, and the second matrix forming component is a crosslinking agent. In some embodiments, the first matrix forming component is a colloid or gelling agent. In some embodiments, the first matrix forming component is a material that is a monomer; and the second matrix forming component is an agent that initiates polymerization of the monomer in the first intermediate coating solution. In some embodiments, the first matrix forming component is a first monomer; and the second matrix forming component is a second monomer, such that when the first monomer and second monomers are mixed, a copolymer is formed.

In yet other embodiments is a kit comprising a first intermediate coating solution comprising an enzyme and a first matrix forming component; and a second intermediate coating solution comprising a second matrix forming component and dye or stain. In some embodiments, the dye or stain includes at least a portion which is a substrate for the enzyme, such that the enzyme may act upon the substrate portion of dye or stain to produce a precipitate. In some embodiments, the dye or stain is DAB and the enzyme (e.g. horseradish peroxidase) is one that acts upon DAB to provide a chromogenic precipitate. In some embodiments, the first matrix forming component is a material that is capable of crosslinking, and the second matrix forming component is a crosslinking agent. In some embodiments, the first matrix forming component is a colloid or gelling agent. In some embodiments, the first matrix forming component is a material that is a monomer; and the second matrix forming component is an agent that initiates polymerization of the monomer in the first intermediate coating solution. In some embodiments, the first matrix forming component is a first monomer; and the second matrix forming component is a second monomer, such that when the first monomer and second monomers are mixed, a copolymer is formed. In some embodiments, the first intermediate coating solution comprises horseradish peroxidase and gelatin; and the second intermediate coating solution comprises DAB and a crosslinking agent (e.g. glutaraldehyde). In other embodiments, the first intermediate coating solution comprises horseradish peroxidase, gelatin, hydrogen peroxide; and the second intermediate coating solution comprises DAB and a crosslinking agent. In some embodiments, the kit further comprises a third intermediate coating solution comprising a second staining reagent (e.g. copper).

In further embodiments is a kit comprising a first intermediate coating solution comprising an enzyme and a first matrix forming component; a second intermediate coating solution comprising a dye or stain; and a third intermediate coating solution comprising a second matrix forming component. In some embodiments, the first and second intermediate coating solutions may be mixed together to provide a mixed coating solution and then applied to a substrate. Subsequently, the third intermediate coating solution may be applied to the mixed coating solution to form a matrix. In some embodiments, the first matrix forming component is a colloid or gelling agent. In some embodiments, the first matrix forming component is a material that is a monomer; and the second matrix forming component is an agent that initiates polymerization of the monomer in the first intermediate coating solution. In some embodiments, the first matrix forming component is a first monomer; and the second matrix forming component is a second monomer, such that when the first monomer and second monomers are mixed, a copolymer is formed. In some embodiments, the first intermediate coating solution comprises horseradish peroxidase and gelatin; and the second intermediate coating solution comprises DAB; and the third intermediate coating solution comprises a crosslinking agent (e.g. glutaraldehyde).

In some embodiments is a kit comprising a plurality of different coating solutions, where each different coating solution of the plurality of different coating solutions comprises a different concentration of dye or stain (an example is set forth in the Table 1 which follows). In some embodiments, the kit further comprises a plurality of substrates to which each of the different coating solutions may be independently applied.

TABLE 1

| Set # | Set 1 | | Set 2 | | Set 3 | | Set 4 | | Set 5 | |
|---|---|---|---|---|---|---|---|---|---|---|
| Tube | 1 | 2 | 3 | 4 | 5 | 6 | 7 | 8 | 9 | 10 |
| Dye or stain (Relative concentration amount) | 1x | | 5x | | 10x | | 15x | | 20x | |
| Enzyme | | x | | x | | x | | x | | x |
| Gelling Agent | | x | | x | | x | | x | | x |

Example 1—Effect of Light Extinction on DAB Concentration

Figure 10:
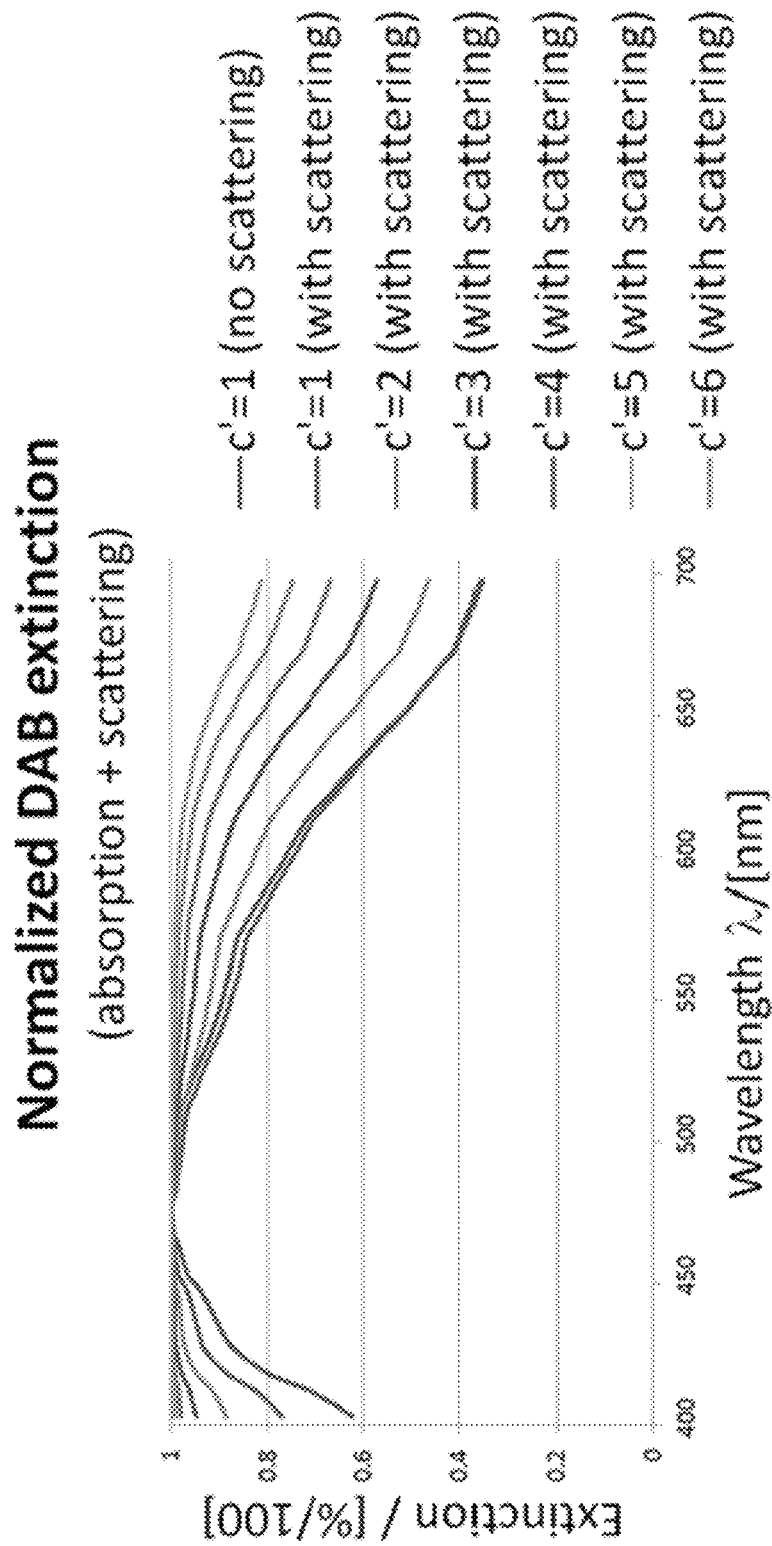
FIG. 10 illustrates the extinction of DAB at various concentrations, i.e. at various precipitate concentrations.

The Beer-Lambert equation assumes small stain concentrations and no interaction between the absorbing molecules. In other words, it is assumed that the absorption factor $c_R$, $c_G$ and $c_B$ are the only factors to impact the light extinction, which are independent of stain concentration. However, this assumption does not hold well for DAB stain due to its precipitate-forming reaction during sample processing. Light scattering needs to be taken into consideration, which causes the light extinction (i.e., absorption+scattering) to be concentration-dependent. FIG. 10 illustrates the effect of stain concentration on extinction (see Peter H. and Tobias M., "Supplementary Information to A model-based survey of color deconvolution in diagnostic bright field microscopy: Error Estimation and Spectral Consideration," Sci Rep. 2015; 5: 12096).

As shown, for a given concentration, the peak extinction (which is used as the normalization factor) occurs at about 475 nm, which roughly corresponds to the center of the blue spectral band. The red spectral band, which covers the higher wavelengths, has the least extinction when compared to the peak. The extinction of green spectral band is in-between. As the stain concentration increases, the ratio to the peak extinction across different wavelengths is generally increased for wavelengths higher than about 475 nm. This means that the proportions of RGB channel signals in the detected light change due to increased scattering along with the stain concentration variations. Therefore, different OD vectors are needed to characterize DAB stain at different concentrations.

Example 2—Method of Preparing a DAB Slide with Controlled Concentrations (Reference Color Set Generation)

To study the chromatic characteristic of DAB stain at different concentration levels, DAB slides with controlled concentrations are generated. Considering that tissue sample will introduce significant intra-slide variations of DAB concentration, a special slide preparation process has been developed to generate slide with uniform DAB concentration distribution. This helps to extract reliable reference color vector for a particular concentration level.

DAB reagent: 48.5 mM diaminobenzidine, 5 mM Sodium metabisulfite, 0.5% (w/v) polyethylenimine $H_2O_2$ reagent: 118 mM $H_2O_2$, 385 mM potassium phosphate dibasic, trihydrate, 115 mM potassium phosphate monobasic, pH 7.3, 240 mM sodium chloride, 700 mM imidazole, 700 mM 2-hydroxypyridine, 0.25% (w/v) Brij-35

Gelatin, 50 bloom (MP Biomedicals)
OptiView anti-HQ HRP (Ventana Medical Systems, Inc.)
OptiView Copper (Ventana Medical Systems, Inc.)
Glutaraldehyde solution, Grade I (Sigma-Aldrich)

For gel preparation, a solution of 3% (w/v) gelatin in DI $H_2O$ was made. This solution was dissolved by heating to 70° C. with occasional stirring. Once the solution was dissolved, 300 μL of it was removed and cooled to 37° C. for 5 minutes.

While the gel solution cooled, the other reagents were warmed to 37° C. Once everything was equilibrated to 37° C. 100 μL OptiView anti-HQ HRP was mixed with the gelatin aliquot. In a separate tube, 300 μL DAB and 300 μL $H_2O_2$ were mixed, then the mixture was added to the gelatin+anti-HQ HRP mixture and the whole solution was mixed thoroughly. Finally, 100 μL OptiView Copper reagent was added to the mixture and everything was mixed again.

300 μL of this gelatin mixture was pipetted onto the non-frosted portion of a clear SuperFrost Plus slide. The slide was carefully tilted in an orbital motion to ensure the gelatin mixture fully and evenly covered the non-frosted portion of the slide. The slide was placed horizontally on a surface cooled to 4° C. and incubated for 3 minutes to set the gel. Once the gel was set, 50 μL of glutaraldehyde was applied to the surface of the hardened DAB gel and a glass 1.5 mm coverslip was immediately placed on the gel to spread the glutaraldehyde across the entire DAB gel surface. The slide was then incubated at room temperature for 3 minutes while the glutaraldehyde diffused into the gel and crosslinked the gelatin particles. After 3 minutes excess fluid from the edges of the slide was carefully wiped away. Clear acrylic sealer was applied to the edges of the coverslip and the slide in order to attach the coverslip to the slide and seal the DAB gel against moisture loss.

Figure 11:
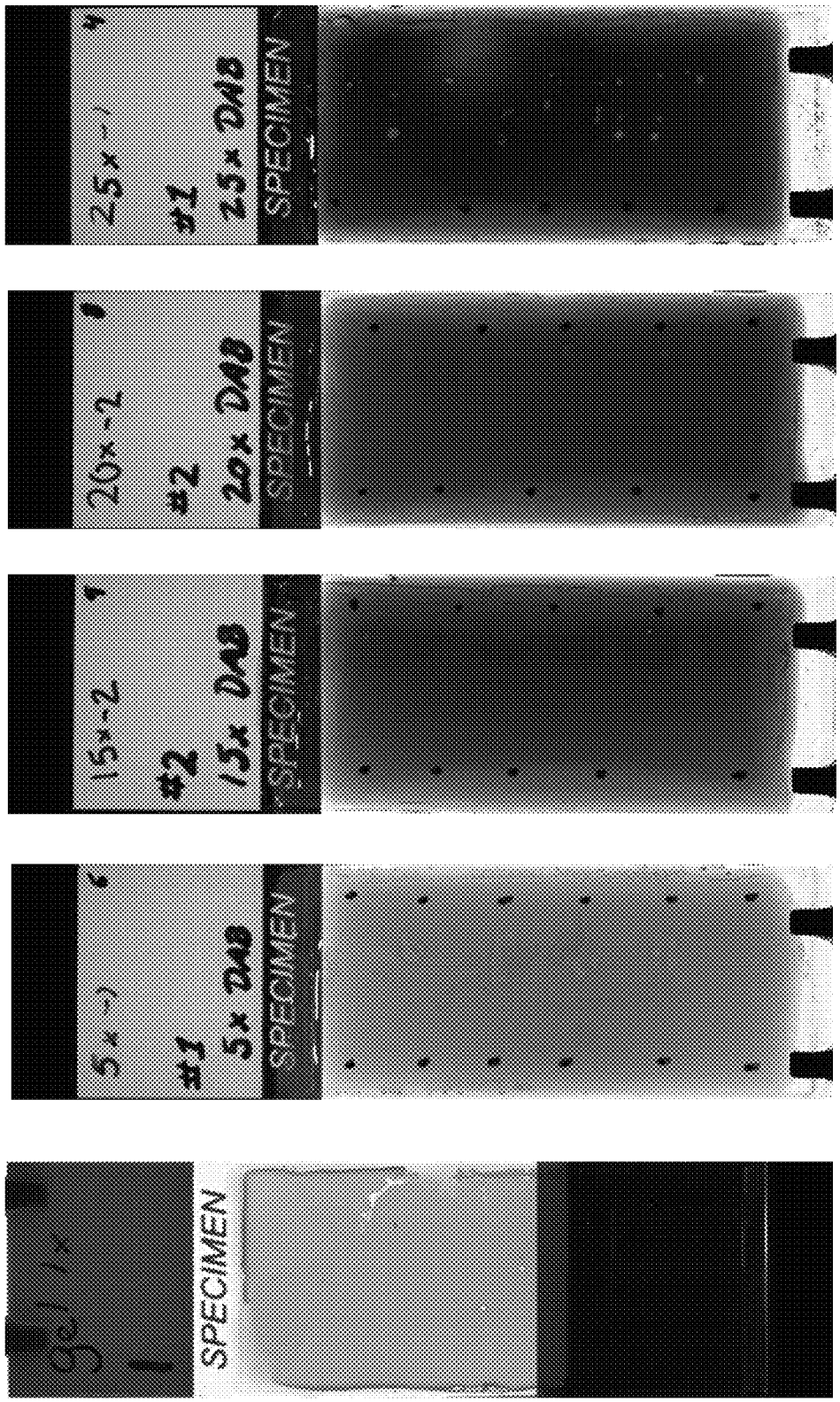
FIG. 11 illustrates five slides prepared using different concentrations of DAB, where (a) 1×, (b) 5×, (c) 15×, (d) 20×, (e) 25×, which are relative to OptiView (Ventana Medical Systems, Inc.) on-slide concentrations of approximately 1.9 mM DAB.
Figure 12A:
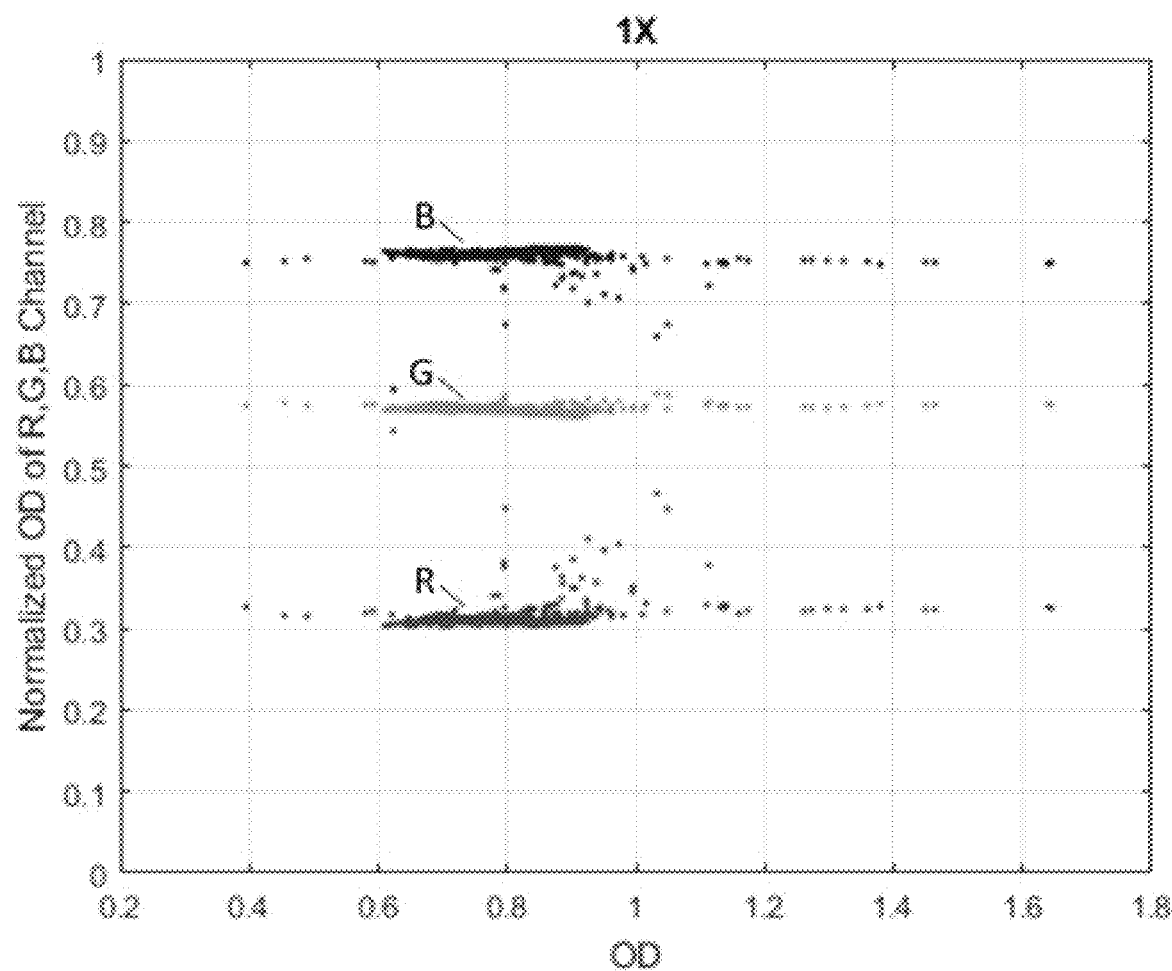
FIGS. 12A-12E illustrate normalized OD values for each RGB channel vs. the total OD value for slides processed using an anti-Vimentin IHC protocol. The red (R), green (G) and blue (B) colored dots are used to represent RGB channels, respectively. The samples are randomly selected from each of the 1000×1000 FOVs which cover the tissue.
Figure 12B:
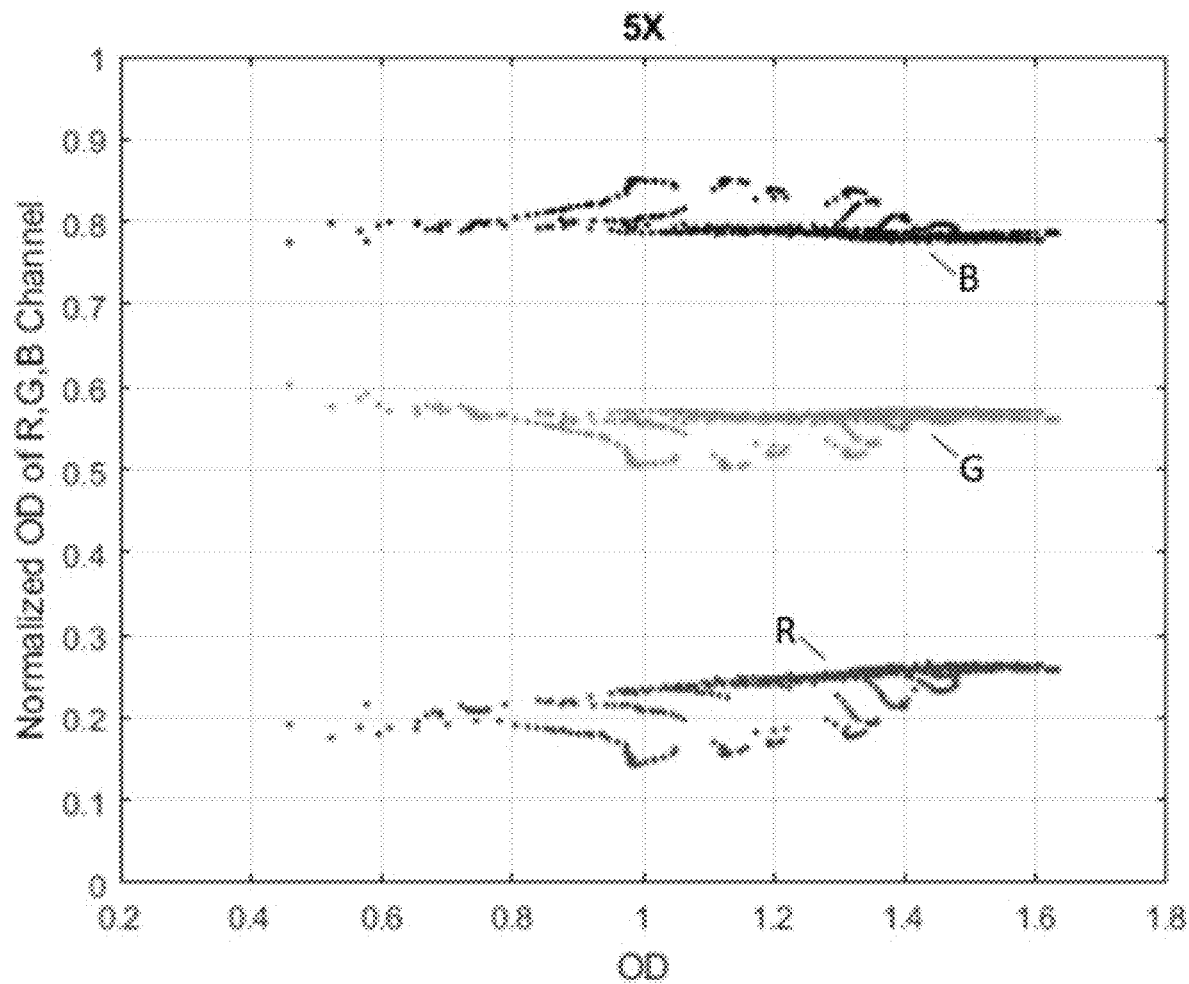
Figure 12C:
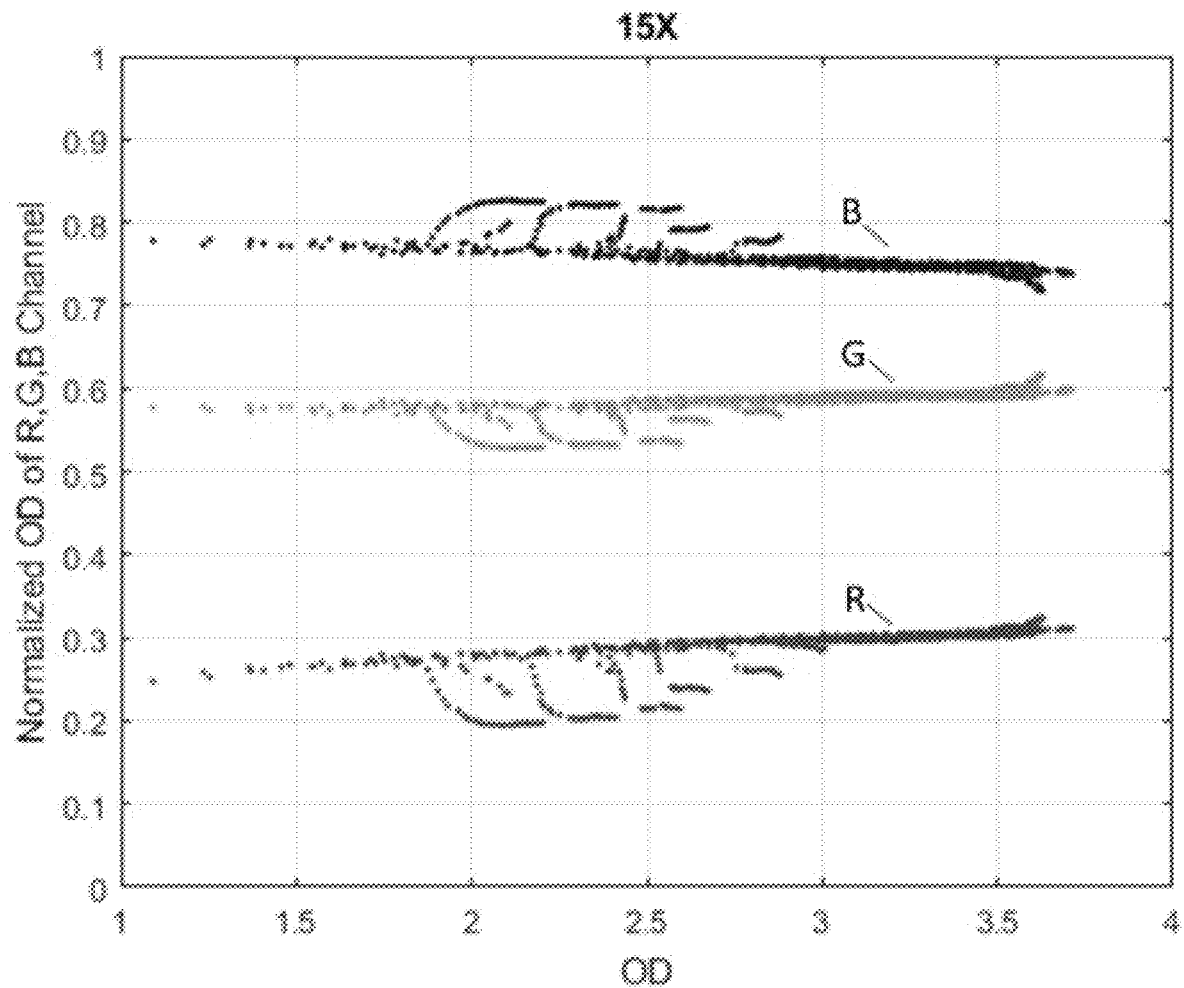
Figure 12D:
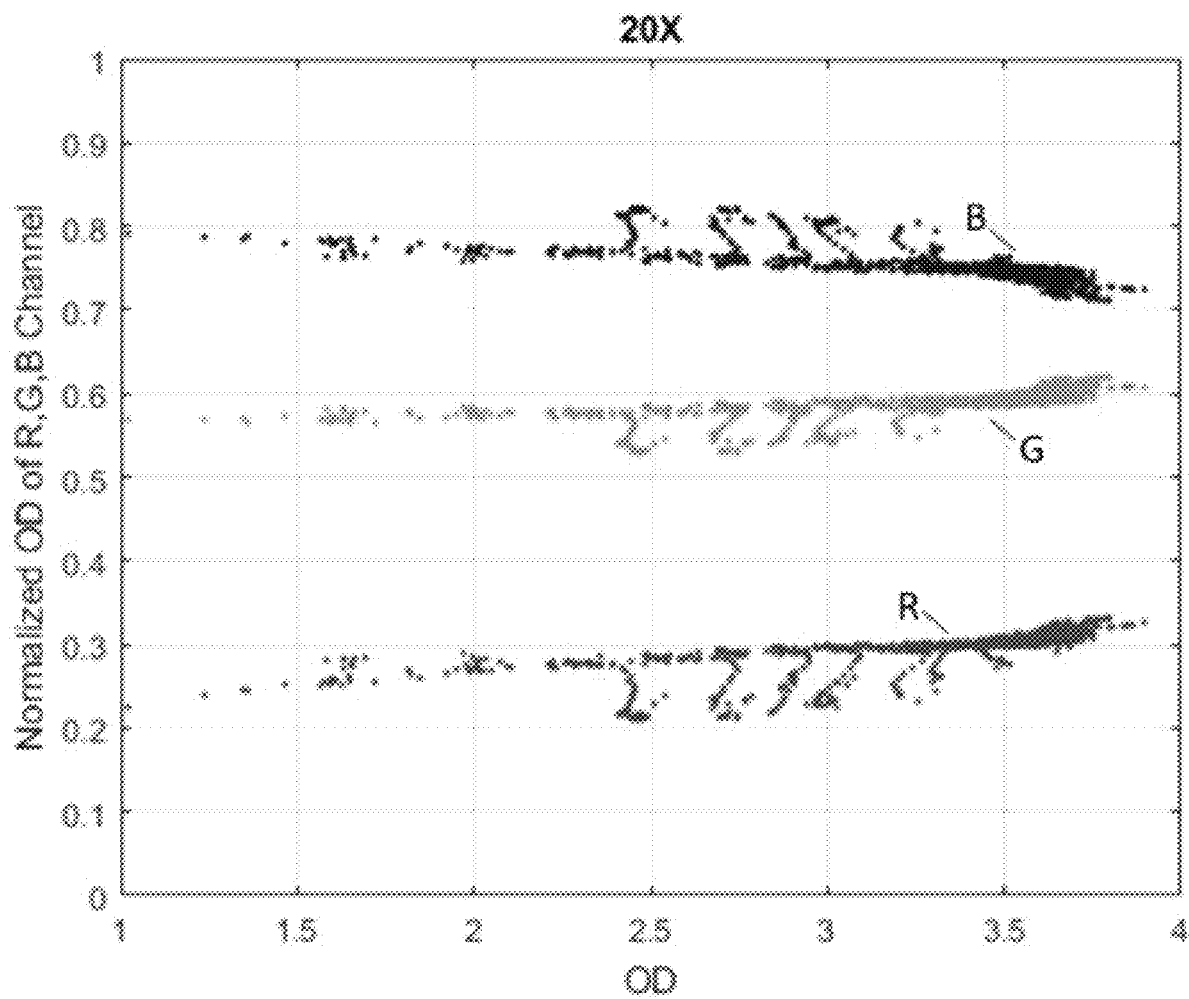
Figure 12E:
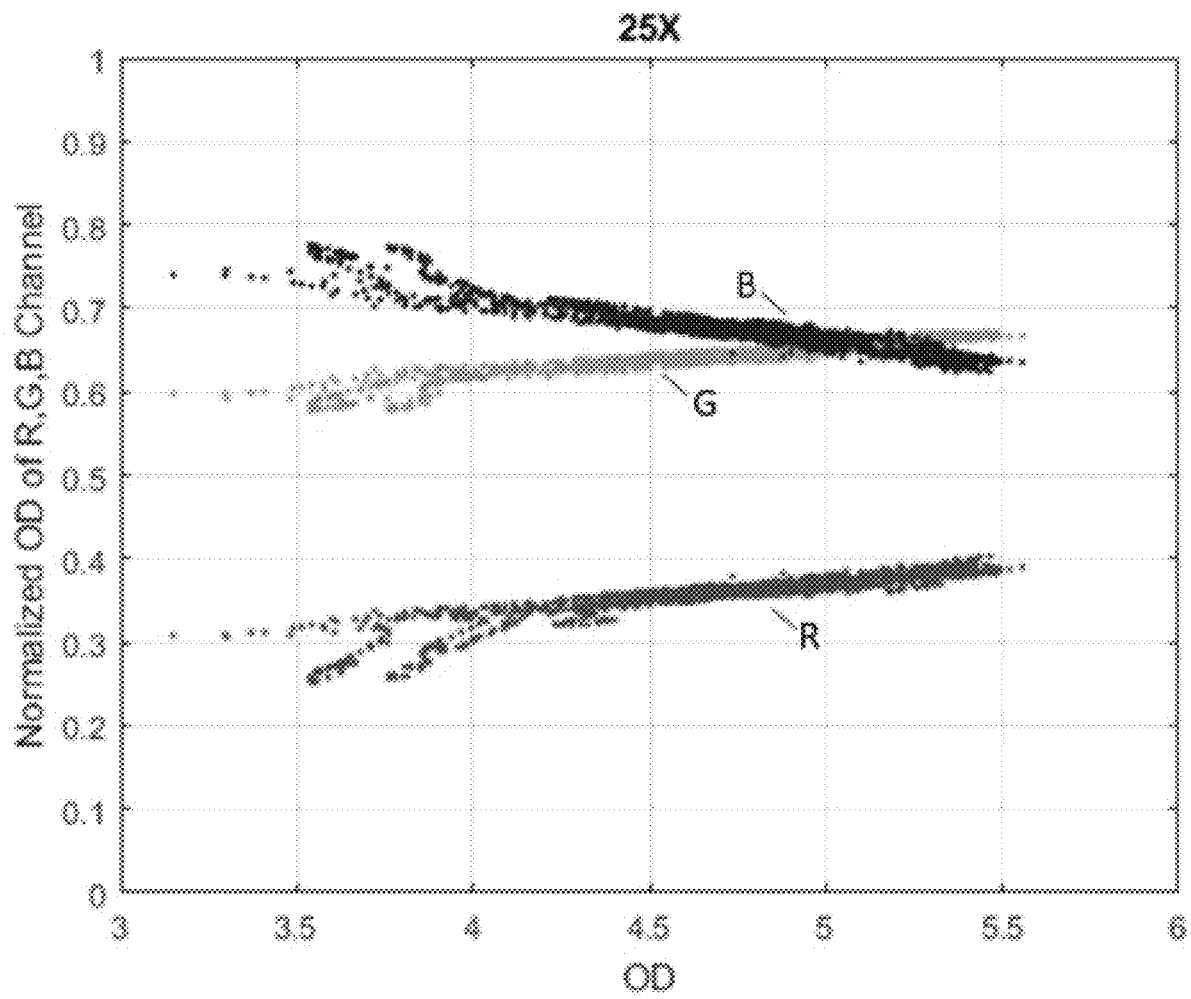

To visualize the chromatic characteristic of DAB at different concentration levels, the sample slides were scanned and the average optical density vector of each 1000×1000 field of view (FOV) were computed for each slide. The normalized optical density values for each RGB channel were plotted against the total optical density value for all the FOVs within a slide. Note that the total optical density value equals the length of the average optical density vector for each FOV, which indicates the stain concentration. FIG. 11 provides thumbnail images of the sample slides prepared using the disclosed method. The concentrations are (a) 1×, (b) 5×, (c) 15×, (d) 20×, (e) 25×, which are relative to OptiView on-slide concentrations of about 1.9 mM DAB.

Example 3—Coating Composition Components

Table 2 below sets forth the various components and their relative amounts in five different coating compositions. Each coating composition comprises the same components, but vary in the amounts of the components present, e.g. the amount of DAB present.

TABLE 2

| Reagents | 1x DAB concentration | | 5x DAB concentration | | 15x DAB concentration | | 20x DAB concentration | | 25x DAB concentration | |
| --- | --- | --- | --- | --- | --- | --- | --- | --- | --- | --- |
| | concen., mM | % | concen., mM | % | concen., mM | % | concen., mM | % | concen., mM | % |
| DAB reagent | | | | | | | | | | |
| diaminobenzidine | 1.9 | 0.106 w/v | 9.5 | 0.531 w/v | 28.5 | 1.59 w/v | 38 | 2.12 w/v | 47.5 | 2.66 w/v |
| sodium metabisulfite | 0.2 | 0.00992 w/v | 1 | 0.0496 w/v | 3 | 0.149 w/v | 4 | 0.198 w/v | 5 | 0.248 w/v |
| polyethylenimine MW 25000, linear | 0.0209 | 0.00622 w/v | 0.104 | 0.0261 w/v | 0.313 | 0.0783 w/v | 0.417 | 0.104 w/v | 0.522 | 0.13 w/v |
| H2O2 reagent | | | | | | | | | | |
| H2O2 | 118 | 1.05 v/v | 118 | 1.05 v/v | 118 | 1.05 v/v | 118 | 1.05 v/v | 118 | 1.05 v/v |
| potassium phosphate dibasic trihydrate | 385 | 22.9 w/v | 385 | 22.9 w/v | 385 | 22.9 w/v | 385 | 22.9 w/v | 385 | 22.9 w/v |
| potassium phosphate monobasic | 115 | 4.08 w/v | 115 | 4.08 w/v | 115 | 4.08 w/v | 115 | 4.08 w/v | 115 | 4.08 w/v |
| sodium chloride | 240 | 3.66 w/v | 240 | 3.66 w/v | 240 | 3.66 w/v | 240 | 3.66 w/v | 240 | 3.66 w/v |
| imidazole | 700 | 12.4 w/v | 700 | 12.4 w/v | 700 | 12.4 w/v | 700 | 12.4 w/v | 700 | 12.4 w/v |
| 2-hydroxypyridine | 700 | 17.4 w/v | 700 | 17.4 w/v | 700 | 17.4 w/v | 700 | 17.4 w/v | 700 | 17.4 w/v |
| Brij-35, 30% solution | 5.44 | 0.0652 v/v | 5.44 | 0.0652 v/v | 5.44 | 0.0652 v/v | 5.44 | 0.0652 v/v | 5.44 | 0.0652 v/v |
| OptiView anti-HQ HRP | | | | | | | | | | |
| OptiView anti-HQ HRP | — | 0.087 v/v | — | 0.087 v/v | — | 0.087 v/v | — | 0.087 v/v | — | 0.087 v/v |
| OptiView Copper | | | | | | | | | | |
| OptiView Copper | — | 0.087 v/v | — | 0.087 v/v | — | 0.087 v/v | — | 0.087 v/v | — | 0.087 v/v |
| Glutaraldehyde | | | | | | | | | | |
| glutaraldehyde solution (25%), grade 1 | 43.4 | 0.0435 v/v | 43.4 | 0.0435 v/v | 43.4 | 0.0435 v/v | 43.4 | 0.0435 v/v | 43.4 | 0.0435 v/v |
| Gelatin | | | | | | | | | | |
| gelatin, 50 bloom | 3.91 | 0.783 w/v | 3.91 | 0.783 w/v | 3.91 | 0.783 w/v | 3.91 | 0.783 w/v | 3.91 | 0.783 w/v |

Example 4—Impact of DAB Concentration to the Optical Density Vectors

To visualize the impact of DAB concentration to the optical density vectors, the average optical density vector for a 1000×1000 FOV on each slide were computed. The normalized optical density values were plotted for each RGB channel against the total optical density value for all the FOVs within a slide. Note that the total optical density value equals the length of the average optical density vector for each FOV, which indicates the stain concentration. FIGS. 12A-12E show the results for the 5 slides as shown in FIG. 11.

As seen, $OD_R < OD_G < OD_B$ are observed for slides IX, 5×, 15×, 20×, which is consistent with the DAB extinction plot as shown in FIG. 10. Moreover, the normalized $OD_R$, $OD_G$, $OD_B$ values generally remain constant in the low total OD value range, indicating that the Beer-Lambert's law holds reasonably well for low DAB concentrations. Decreasing of normalized OD B and increasing of normalized $OD_R$ and $OD_G$ are observed as the total OD value increases, especially when the total OD value is greater than 3. The trend is the most obvious for slide 25×, indicating strong scattering effects for high DAB concentrations. The reference color vector for each concentration level is generated by taking the average normalized OD vector for each slide (excluding the artifacts area).

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary, to employ concepts of the various patents, applications and publications to provide yet further embodiments.

Although the present disclosure has been described with reference to a number of illustrative embodiments, it should be understood that numerous other modifications and embodiments can be devised by those skilled in the art that will fall within the spirit and scope of the principles of this disclosure. More particularly, reasonable variations and modifications are possible in the component parts and/or arrangements of the subject combination arrangement within the scope of the foregoing disclosure, the drawings, and the appended claims without departing from the spirit of the disclosure. In addition to variations and modifications in the component parts and/or arrangements, alternative uses will also be apparent to those skilled in the art.

The invention claimed is:

1. A calibration system comprising:
   (a) an optically transparent substrate;
   (b) a film having a substantially uniform thickness disposed on at least a portion of the optically transparent substrate, the film comprising a chromogenic precipitate embedded within a polymer, wherein the chromogenic precipitate is uniformly dispersed within the polymer.

2. The calibration system of claim 1, wherein the polymer is a hydrogel.

3. The calibration system of claim 2, wherein the hydrogel comprises crosslinked gelatin.

4. The calibration system of claim 3, wherein the crosslinked gelatin is derived from gelatin and an aldehyde.

5. The calibration system of claim 2, wherein the hydrogel is derived from a gelling agent and a crosslinking agent.

6. The calibration system of claim 1, wherein the polymer is an acrylate.

7. The calibration system of claim 1, wherein the chromogenic precipitate is a reaction product of a chromogen and an enzyme.

8. The calibration system of claim 7, wherein the chromogen is selected from the group consisting of 5-Bromo-4-Chloro-3-Indolyl Phosphate; 4-Chloro-2-methyl benzenediazonium; 3,3'-Diaminobenzidine; 3,3',5,5;-tetramethylbenzidine; 4-chloro-1-naphthol; 2,2'-azino-bis (3-ethylbenzothiazoline-6-sulphonic acid); o-phenylenediamine dihydrochloride; p-Nitrophenyl Phosphate; 5-Bromo-4-Chloro-3-indolyl-B-D-Galactopyranoside; and 2,2,5-5-tetra-p-nitrophenyl-3,3-(3,3-dimethoxy-4,4-biphenylene)-di tetrazolium chloride.

9. The calibration system of claim 8, wherein the chromogen is 3,3'-Diaminobenzidine.

10. The calibration system of claim 8, wherein the enzyme is selected from the group consisting of alkaline phosphatase, horseradish peroxidase, glycosylases, and glucose oxidase.

11. The calibration system of claim 1, wherein a ratio of the chromogenic precipitate to the polymer ranges from about 0.1 to about 50.

12. A set of slides comprising:
   (a) a first slide having a first coating disposed on at least a portion of an upper surface of the first slide, the first coating comprising a stain present in a polymeric matrix at a first concentration;
   (b) a second slide having a second coating disposed on at least a portion of an upper surface of the second slide, the second coating comprising the stain present in the polymeric matrix at a second concentration;
   wherein the first concentration and the second concentration are different.

13. The set of slides of claim 12, wherein the stain is a chromogenic precipitate.

14. The set of slides of claim 13, wherein the chromogenic precipitate is derived from one of 5-Bromo-4-Chloro-3-Indolyl Phosphate; 4-Chloro-2-methyl benzenediazonium; 3,3'-Diaminobenzidine; 3,3',5,5;-tetramethylbenzidine; 4-chloro-1-naphthol; 2,2'-azino-bis(3-ethylbenzothiazoline-6-sulphonic acid); o-phenylenediamine dihydrochloride; p-Nitrophenyl Phosphate; 5-Bromo-4-Chloro-3-indolyl-B-D-Galactopyranoside; or 2,2,5-5-tetra-p-nitrophenyl-3,3-(3, 3-dim ethoxy-4,4-biphenylene)-di tetrazolium chloride.

15. The set of slides of claim 12, wherein the second concentration is at least twice the first concentration.

16. A kit comprising:
   (i) a first set of coating reagents comprising:
      a. a first intermediate coating solution comprising a first matrix forming component and an enzyme; and
      b. a second intermediate coating solution comprising a chromogen, wherein the chromogen is present in the second intermediate coating solution at a first concentration; and
   (ii) a second set of coating reagents comprising
      a. a third intermediate coating solution comprising the first matrix forming component and the enzyme; and
      b. a fourth intermediate coating solution comprising the chromogen, wherein the chromogen is present in the fourth intermediate coating solution at a second concentration.

17. The kit of claim 16, further comprising a fifth intermediate coating solution comprising a crosslinking reagent.

18. The kit of claim 16, wherein the chromogen is selected from the group consisting of 5-Bromo-4-Chloro-3-Indolyl Phosphate; 4-Chloro-2-methyl benzenediazonium; 3,3'-Diaminobenzidine; 3,3',5,5;-tetramethylbenzidine; 4-chloro-1- naphthol; 2,2'-azino-bis(3-ethylbenzothiazoline-6-sulphonic acid); o-phenylenediamine dihydrochloride; p-Nitrophenyl Phosphate; 5-Bromo-4-Chloro-3-indolyl-B-D-Galactopyranoside; and 2,2,5-5-tetra-p-nitrophenyl-3,3-(3,3-dimethoxy-4,4-biphenylene)-di tetrazolium chloride.

19. The kit of claim 16, wherein the chromogen is 3,3'-Diaminobenzidine.

20. The kit of claim 18, wherein the enzyme is selected from the group consisting of alkaline phosphatase, horseradish peroxidase, glycosylases, and glucose oxidase.

* * * * *